US011953479B2

(12) United States Patent
Schmitt et al.

(10) Patent No.: US 11,953,479 B2
(45) Date of Patent: Apr. 9, 2024

(54) SELECTIVE OPTICAL AQUEOUS AND NON-AQUEOUS DETECTION OF FREE SULFITES

(71) Applicant: The Research Foundation for the State University of New York, Binghamton, NY (US)

(72) Inventors: Lynn Schmitt, Binghamton, NY (US); Alistair Lees, Binghamton, NY (US)

(73) Assignee: The Research Foundation for The State University of New York, Binghamton, NY (US)

( * ) Notice: Subject to any disclaimer, the term of this patent is extended or adjusted under 35 U.S.C. 154(b) by 919 days.

(21) Appl. No.: 16/753,906

(22) PCT Filed: Oct. 5, 2018

(86) PCT No.: PCT/US2018/054770
§ 371 (c)(1),
(2) Date: Apr. 6, 2020

(87) PCT Pub. No.: WO2019/071240
PCT Pub. Date: Apr. 11, 2019

(65) Prior Publication Data
US 2020/0363382 A1 Nov. 19, 2020

Related U.S. Application Data

(60) Provisional application No. 62/569,193, filed on Oct. 6, 2017.

(51) Int. Cl.
*G01N 31/22* (2006.01)
*C07D 401/04* (2006.01)
(Continued)

(52) U.S. Cl.
CPC .......... *G01N 31/22* (2013.01); *C07D 401/04* (2013.01); *G01N 21/78* (2013.01); *G01N 33/14* (2013.01)

(58) Field of Classification Search
CPC ......... G01N 31/22; G01N 21/78; G01N 33/14
See application file for complete search history.

(56) References Cited

U.S. PATENT DOCUMENTS

| 5,962,215 A | 10/1999 | Douglas et al. |
| 6,406,862 B1 | 6/2002 | Krakauer |

(Continued)

FOREIGN PATENT DOCUMENTS

JP 10324687 12/1998

OTHER PUBLICATIONS

Selective optical aqueous anion detection by 4-pyrrolylpyridine Lynn Schmitt, Alistair Lees 41st Northeast Regional Meeting of the American Chemical Society, Oct. 5, 2016 (Year: 2016).*

*Primary Examiner* — Brian R Gordon
*Assistant Examiner* — Dwan A Gerido
(74) *Attorney, Agent, or Firm* — Hoffberg & Associates; Steven M. Hoffberg

(57) ABSTRACT

4-pyrrolylpyridine, a novel anion sensor, displays a substantial color loss upon addition of sodium sulfite in aqueous solvents. A variety of anions were tested, including halides, phosphates, sulfates, and hydroxide, but all solutions remained unchanged aside from the sulfite, which displayed bleaching. Described here is a method for which the exact concentration of sulfites in a consumer product can be determined. The test is sensitive over a broad range of sulfites, from 0.84 ppm to over 10,000 ppm, and is accurate with a standard deviation of ±0.01 ppm.

20 Claims, 4 Drawing Sheets

(51) Int. Cl.
*G01N 21/78* (2006.01)
*G01N 33/14* (2006.01)

(56) References Cited

U.S. PATENT DOCUMENTS

| | | |
|---|---|---|
| 6,818,180 B2 | 11/2004 | Douglas et al. |
| 7,087,397 B2 | 8/2006 | Anaokar et al. |
| 7,229,783 B2 | 6/2007 | Saul et al. |
| 7,280,201 B2 | 10/2007 | Helbing |
| 7,282,349 B2 | 10/2007 | Lye |
| 7,504,235 B2 | 3/2009 | Song |
| 7,674,615 B2 | 3/2010 | Ramel |
| 7,846,383 B2 | 12/2010 | Song |
| 8,003,399 B2 | 8/2011 | Song et al. |
| 8,380,541 B1 | 2/2013 | Holmes |
| 8,383,047 B2 | 2/2013 | Obeid et al. |
| 8,470,609 B2 | 6/2013 | Chen |
| 8,475,731 B2 | 7/2013 | Abraham et al. |
| 8,574,919 B2 | 11/2013 | Ramel et al. |
| 8,623,292 B2 | 1/2014 | Song et al. |
| 8,642,355 B2 | 2/2014 | Chen |
| 8,901,366 B2 | 12/2014 | Song et al. |
| 9,016,193 B2 | 4/2015 | Minvielle |
| 9,149,806 B2 | 10/2015 | Collins |
| 9,186,278 B2 | 11/2015 | Baym et al. |
| 9,228,953 B2 | 1/2016 | Karlsson et al. |
| 9,230,185 B1 | 1/2016 | Berry et al. |
| 9,241,663 B2 | 1/2016 | Jena et al. |
| 9,390,312 B2 | 7/2016 | Bangera et al. |
| 9,445,749 B2 | 9/2016 | Erickson et al. |
| 9,456,777 B2 | 10/2016 | Bangera et al. |
| 9,476,159 B2 | 10/2016 | France et al. |
| 9,506,855 B2 | 11/2016 | Papautsky et al. |
| 9,526,450 B2 | 12/2016 | Baym et al. |
| 9,526,480 B2 | 12/2016 | Baym et al. |
| 9,549,703 B2 | 1/2017 | Baym et al. |
| 9,552,529 B2 | 1/2017 | Berry et al. |
| 9,557,331 B2 | 1/2017 | Bangera et al. |
| 9,563,833 B2 | 2/2017 | Swager et al. |
| 9,569,858 B2 | 2/2017 | Babcock et al. |
| 9,610,037 B2 | 4/2017 | Baym et al. |
| 9,619,627 B2 | 4/2017 | Holmes |
| 9,686,395 B2 | 6/2017 | Erickson et al. |
| 9,731,391 B2 | 8/2017 | Souza et al. |
| 2001/0039057 A1 | 11/2001 | Douglas et al. |
| 2002/0085069 A1 | 7/2002 | Anagnostopoulos et al. |
| 2002/0101486 A1 | 8/2002 | Anagnostopoulos |
| 2003/0007039 A1 | 1/2003 | Lebens et al. |
| 2003/0067516 A1 | 4/2003 | Lebens et al. |
| 2003/0116257 A1 | 6/2003 | Franklin et al. |
| 2003/0175153 A1 | 9/2003 | Anaokar et al. |
| 2004/0028608 A1 | 2/2004 | Saul et al. |
| 2004/0127883 A1 | 7/2004 | Cowell et al. |
| 2005/0130253 A1 | 6/2005 | Ye et al. |
| 2005/0223983 A1 | 10/2005 | Selvamanickam et al. |
| 2006/0008847 A1 | 1/2006 | Ramel et al. |
| 2006/0115580 A1 | 6/2006 | Selvamanickam et al. |
| 2006/0132786 A1 | 6/2006 | Helbing |
| 2006/0275920 A1 | 12/2006 | Petrilla et al. |
| 2006/0292040 A1 | 12/2006 | Wickstead et al. |
| 2007/0048182 A1 | 3/2007 | Song et al. |
| 2007/0048815 A1 | 3/2007 | Song |
| 2007/0048816 A1 | 3/2007 | Song |
| 2007/0286771 A1 | 12/2007 | Nunes et al. |
| 2008/0003141 A1 | 1/2008 | Iketani |
| 2008/0057528 A1 | 3/2008 | Sayre et al. |
| 2008/0102473 A1 | 5/2008 | Fouquet et al. |
| 2008/0145945 A1 | 6/2008 | Song |
| 2009/0033727 A1 | 2/2009 | Anagnostopoulos et al. |
| 2009/0068061 A1 | 3/2009 | Chen |
| 2009/0157023 A1 | 6/2009 | Song et al. |
| 2009/0157024 A1 | 6/2009 | Song |
| 2009/0181416 A1 | 7/2009 | Song |
| 2009/0305395 A1 | 12/2009 | Song |
| 2010/0226822 A1 | 9/2010 | Ramel et al. |
| 2010/0284858 A1 | 11/2010 | Ajayaghosh et al. |
| 2010/0290948 A1 | 11/2010 | Song |
| 2010/0311181 A1 | 12/2010 | Abraham et al. |
| 2012/0042722 A1* | 2/2012 | Song .................... G01N 33/558 73/32 R |
| 2013/0080071 A1 | 3/2013 | Holmes |
| 2013/0156286 A1 | 6/2013 | Holmes |
| 2013/0196053 A1 | 8/2013 | Paul et al. |
| 2013/0280725 A1 | 10/2013 | Ismagilov et al. |
| 2013/0295690 A1 | 11/2013 | Chen |
| 2013/0309679 A1 | 11/2013 | Ismagilov et al. |
| 2014/0057255 A1 | 2/2014 | Holmes |
| 2014/0057362 A1 | 2/2014 | Markovsky et al. |
| 2014/0065647 A1 | 3/2014 | Mamenta |
| 2014/0081665 A1 | 3/2014 | Holmes |
| 2014/0120563 A1 | 5/2014 | Ozcan et al. |
| 2014/0147931 A1 | 5/2014 | Chen |
| 2014/0206099 A1 | 7/2014 | Mao et al. |
| 2014/0211204 A1 | 7/2014 | Stedtfeld et al. |
| 2014/0214714 A1 | 7/2014 | Minvielle |
| 2014/0248621 A1 | 9/2014 | Collins |
| 2014/0271362 A1 | 9/2014 | Markovsky et al. |
| 2014/0273270 A1 | 9/2014 | Wang et al. |
| 2014/0286550 A1 | 9/2014 | Beule et al. |
| 2014/0315229 A1 | 10/2014 | Karlsson et al. |
| 2014/0329262 A1 | 11/2014 | Karlsson et al. |
| 2014/0335505 A1 | 11/2014 | Holmes |
| 2014/0356864 A1 | 12/2014 | Khan |
| 2015/0055134 A1 | 2/2015 | Papautsky et al. |
| 2015/0091233 A1 | 4/2015 | Souza et al. |
| 2015/0116093 A1 | 4/2015 | Swager et al. |
| 2015/0126947 A1 | 5/2015 | Stabelfeldt et al. |
| 2015/0227887 A1 | 8/2015 | Minvielle |
| 2015/0244852 A1 | 8/2015 | Erickson et al. |
| 2015/0247190 A1 | 9/2015 | Ismagilov et al. |
| 2015/0247874 A1 | 9/2015 | Chavez Benavides et al. |
| 2015/0291628 A1 | 10/2015 | Danaboyina et al. |
| 2015/0291966 A1 | 10/2015 | Zhang et al. |
| 2015/0293091 A1 | 10/2015 | Slusarewicz et al. |
| 2015/0293115 A1 | 10/2015 | Buhimschi et al. |
| 2015/0310634 A1 | 10/2015 | Babcock et al. |
| 2015/0325006 A1 | 11/2015 | Adiri et al. |
| 2015/0359458 A1 | 12/2015 | Erickson et al. |
| 2016/0008809 A1 | 1/2016 | Li et al. |
| 2016/0025715 A1 | 1/2016 | DiMagno et al. |
| 2016/0038936 A1 | 2/2016 | Ding et al. |
| 2016/0076083 A1 | 3/2016 | Ellington et al. |
| 2016/0080548 A1 | 3/2016 | Erickson et al. |
| 2016/0117565 A1 | 4/2016 | Berry et al. |
| 2016/0161415 A1 | 6/2016 | Robinson et al. |
| 2016/0167051 A1 | 6/2016 | Collins |
| 2016/0171690 A1 | 6/2016 | Adiri et al. |
| 2016/0239624 A1 | 8/2016 | Short et al. |
| 2016/0263577 A1 | 9/2016 | Ismagilov et al. |
| 2016/0273154 A1 | 9/2016 | France et al. |
| 2016/0283706 A1 | 9/2016 | Holmes |
| 2016/0289750 A1 | 10/2016 | Landegren et al. |
| 2016/0291000 A1 | 10/2016 | Filipe et al. |
| 2016/0319354 A1 | 11/2016 | Tocigl et al. |
| 2016/0327473 A1 | 11/2016 | Ozcan et al. |
| 2016/0374600 A1 | 12/2016 | Short et al. |
| 2017/0000359 A1 | 1/2017 | Kohli et al. |
| 2017/0020436 A1 | 1/2017 | Flament |
| 2017/0022547 A1 | 1/2017 | Chan et al. |
| 2017/0079592 A1 | 3/2017 | Park et al. |
| 2017/0087549 A1 | 3/2017 | Patwardhan |
| 2017/0099415 A1 | 4/2017 | Bell et al. |
| 2017/0102399 A1 | 4/2017 | Mamenta |
| 2017/0166903 A1 | 6/2017 | Zhang et al. |
| 2017/0173262 A1 | 6/2017 | Veltz |
| 2017/0183708 A1 | 6/2017 | Karlsson et al. |
| 2017/0184506 A1 | 6/2017 | Patel |
| 2017/0198329 A1 | 7/2017 | Ayyub et al. |
| 2017/0219576 A1 | 8/2017 | Heavner |
| 2017/0224257 A1 | 8/2017 | Rogers |
| 2017/0231571 A1 | 8/2017 | Rogers et al. |
| 2017/0238854 A1 | 8/2017 | Henshaw |

(56) References Cited

U.S. PATENT DOCUMENTS

| | | |
|---|---|---|
| 2017/0270690 A1 | 9/2017 | Chung et al. |
| 2018/0106524 A1 | 4/2018 | Bates et al. |
| 2018/0143073 A1* | 5/2018 | Goldring .................. G01J 3/42 |

* cited by examiner

Reduction →

SELECTIVE OPTICAL AQUEOUS AND NON-AQUEOUS DETECTION OF FREE SULFITES

FIELD OF THE INVENTION

The present invention relates to the field of optical aqueous anion detection, and more particularly to a sensitive and specific colorimetric sulfite ion detector, suitable for the accurate analytical detection of sulfites in consumer products, such as wine, cider, beer, juices, many foods, chemical solutions, and pharmaceuticals.

BACKGROUND

All references disclosed herein are expressly incorporate herein by reference in their entirety, for all purposes.

Anions are pervasive throughout the natural world, and play fundamental roles in biological, chemical, and environmental processes [1]. Environmentally, they can enhance or diminish plant growth [2]. Biologically, they play key roles in signaling pathways, or may be toxic, causing allergic reactions, skin irritation, and, in some cases, death [3]. One such category of anions, sulfites, are used most widely as a food and beverage preservative that prevent microbial growth and browning [4]. Sulfites in certain doses are toxic, with some people being sensitive to very low levels [5]. More often, a sulfite sensitivity will present as a skin rash or a gastrointestinal problem, but sulfites are notoriously known for inducing asthma attacks and even anaphylaxis [6]. As a result of sulfite's toxicity and ubiquity, legislation has been passed requiring any consumer product containing 10 ppm or more sulfites to label their product as "contains sulfites" [7].

Presently, there are several involved ways in which one can determine the concentration of sulfites in consumer products [8, 9]. Most ways involve pretreatment of the product, and often the addition of strong acids, bases, and oxidizers. Currently the only rapid treatment-free, analytical ways of determining the concentration of free sulfites in beverage, food, and pharmaceuticals are not commercially viable.

Test strips currently on the market require pH adjustment with hazardous sulfuric acid or sodium hydroxide, the use of a pH meter, flammable activated charcoal, and are targeted to the consumer, even though it is difficult if not impossible for a consumer to access such reagents.

Electrochemical based sulfite sensors have a large range of detection limits, typically $1.0 \times 10^{-7}$M to 80 µM. Often these require expensive electrodes comprised of Au, Ru, Cu, Pr, Pt, etc. which are susceptible to fouling. While many can directly measure the concentration of sulfites, they are restricted by their detection limits.

Coumarin based chemodosimeters offer specificity, and have low detection limits (8.3 nM to 50 µM), but they rely on the crosslinking of chromophores which subsequently makes them insoluble in pure water. Consequently, many require co-solvent systems such as DMSO/water, THF/water, DMF/water. Relatively few systems are soluble in pure water.

Titration based testing methods, are limited by the 'ripper test' which can give false positives for red wines and wines containing ascorbic acid, and therefore are not suitable for all wine products, and often have a high degree of error associated with them. Ion Exclusion Chromatography, while accurate, is expensive, complicated, requires a multitude of specialized equipment, as well as a highly-trained chemist.

The optimized Monier-Williams method, sanctioned by the Association of Analytical Chemists, is the method that the Alcohol and Tobacco Tax and Trade Bureau uses to determine concentrations of sulfites in consumer products [7, 31]. This method requires specialized glassware, an inert atmosphere, strong oxidizers, and indicators, among many other chemicals. It also requires several steps and a secondary analysis of the sulfite concentration [32].

There are several test strips on the market, which are reported to provide false positives (incorrect signals or results for sulfites when none are present) when used with foods containing large amounts of ascorbic acid and or tannins [10-12]. These test strips are rendered inaccurate when used without pretreatment of the samples they are meant to be measuring the sulfites concentration in. The development of selective chemosensors for the detection and quantification of sulfites is therefore of utmost importance.

Advantageous characteristics for a sulfite chemosensor would be solubility in water, sensitivity to a broad range of sulfites, optical detection, high selectivity, and not being prone to false positives. Available sulfite sensors either do not function in water or require cellular processes for their function; however, this is not viable when aiming to detect sulfite levels in consumer products [13].

Sulfites are allergens pervasive in food and wine consumer products. Sulfites are added in the form of sulfur dioxide ($SO_2$) for its antimicrobial properties and to prevent food spoilage. This $SO_2$ does not remain in the molecular form and is converted to sulfite ($SO_3^{2-}$) and bisulfite ($HSO_3^-$). Although these products do not have the aforementioned antimicrobial properties, they continue to be allergenic in the body. Sulfites are known to cause a range of symptoms from skin itchiness and rashes to anaphylaxis. Sulfite allergies typically occur in the region of 10 ppm to 500 ppm concentration. The FDA requires product labels with the requirement stating, "Contains Sulfites" at a minimum of 10 ppm. Individuals who have more moderate sensitivities can tolerate some products, but the actual amount of sulfites in a food product is general unknown. While the beer, food, and wine industries test for $SO_2$ levels, these industries do not typically test for $SO_3^{2-}$ and $HSO_3^-$ levels in their products; this is because no affordable and simple test is available.

Definitions

"Aromatic" is defined as an organic compound comprised of double bonds forming flat rings of atoms, and is significantly stabilized by the bonds forming the rings.

"Heterocycle" is an organic compound that is cyclic in shape and composed of atoms other than carbon and hydrogen that are members of its rings.

"Sulfites" are defined as sulfur dioxide, $SO_2$, sulfite, $SO_3^{2-}$, bisulfite, $HSO_3^-$, and metabisulfite, $S_2O_5^{2-}$.

"Anions" are defined as negatively charged atoms or molecules.

"Acid-catalyzed addition reaction" is defined as a chemical reaction when two molecules combine to make a larger molecule, with the reaction being accelerated using acid.

"Covalent Bond" is defined as the sharing of valence electrons between to atoms. "Signaling pathways" are defined as any part of the communication process that determines basic cell activities and cell actions.

"Analyte" is a compound being investigated and measured.

"Chemosensor" or "sensor molecule" is defined as a molecule that interacts with an analyte in a detectable way.

"Synthetic pathway" or "mechanism" is the path that molecules and electrons take when forming a new molecule or molecules.

"Purge" is the removal of air from a system by a light vacuum, and its replacement with another gas.

"Extraction" is defined as a separation process used for purification. This technique separates compounds based on their solubility in two different immiscible liquids.

"Spectroscopy" is defined as measurement of the interaction matter has with electromagnetic radiation.

"Nuclear Magnetic Resonance (NMR) Spectroscopy" is an analytical technique that uses magnetic properties of an atom's nucleus to allow for the determination of the physical and chemical properties of individual atoms in a molecule, and allows for some structural elucidation. An NMR spectrum plots the "chemical shift" or "δ". This is defined as the frequency of light absorbed relative to a standard in a magnetic field.

"Multiplicity" is the splitting of an individual peak into a cluster of peaks in NMR spectroscopy. The splitting arises from an atom's physical and chemical environment.

"UV-Vis Spectroscopy" is defined as spectroscopy that pertains only to the ultraviolet and visible light regions of the electromagnetic spectrum.

"Absorbance" is the logarithm of the ratio of light received by the analyte to the light that is transmitted through the analyte. It is specific to the thickness of the analyte, wavelength, and concentration of analyte.

"Wavelength" is defined as the distance between two successive crests of a wave. "Cuvette" is an optically clear holder for the analyte in a spectrometer.

"Bleach" is defined as the reduction in a peak in an absorption spectrum. "Red-shift" is the moving of spectral lines towards larger wavelengths.

"Ionize" is to convert a molecule or atom into a charged species by either adding or removing electrons.

"Photochemical methods" are defined as methods that are caused by the chemical interaction with light.

"Practical Lower Limit of Quantification" is defined as the limit at which the difference between two values are significant enough to discern the between them. For this test it is defined more specifically as the loss of 10% of the peak intensity at 463 nm.

"Lower Limit of Detection" is defined as the lowest concentration of an analyte that can be distinguished by a reference.

"Buffer" is a solution made of a weak acid and weak base that is resistant to changes in pH.

"Titration" is a technique used to determine the unknown concentration of an analyte by adding measured amounts of the analyte to a standard solution with a known concentration. This is done until a known proportion of a reaction between the analyte and the standard is complete. "Ion Exclusion Chromatography" is a technique for the separation of ionic and non-ionic species in a sample by a column that rejects ionic compounds. As the sample passes through the column, the ionic species are passed through first, and the non-ionic compounds are passed through last.

"Reference" is defined as the components of a solution of the sensor molecule that are not directly involved in the sensing mechanism. When an instrument is referenced, it is calibrated to only record the signal resulting from the sensor molecule.

"Selectivity" is the discrimination of a molecule to quantify an analyte without interference from other compounds that are similar to the analyte. A chemosensor is said to be "selective" if it interacts with only specific analytes.

"Part per million" or "ppm" is a unit of measurement defined as one analyte molecule per million solvent molecules. One ppm is equivalent to 1 mg/1 kg, 1 □L/1 mL, 1 mg/1 L, etc.

"Molarity" or "M" is a unit of concentration defined as the number of moles of solute divided by the volume (L) of solvent.

REFERENCES

[1] Martinez, R.; Sancenon, F.; "Fluorogenic and Chromogenic Chemosensors and reagents for Anions." *Chemical Reviews* 103, 2003, 4419-4476.

[2] Xiaofeng, Y.; Yu, C.; Yexin L.; Zheng, L.; Lijun X.; Ning, Y.; Zheng L.; Lu, J.; Zhang, G.; Liu, C.; Zhang, G.; "A new diketopyrrolopyrrole-based probe for sensitive and selective detection of sulfite in aqueous solution." *Spectrochimica Acta Part A: Moleadar and Biomolecular Spectrscopy* 137,2015, 1055-1060.

[3] Ishii, A.; Seno, H.; Watanabe-Suzuki, K.; Suzuki, O.; Kumazawa, T.; "Determination of Cyanide in Whole Blood by Capillary Gas Chromatography with Cryogenic Oven Trapping." *Analytical Chemisty* 70, 1998, 4873-4876.

[4] Freedman, B.; "Sulphur dioxide in foods and beverages: Its use as a preservative and its effect on asthma." *British Journal of Diseases of the Chest,* 74, 1980, 128-134.

[5] Vally, H.; Thompson, P. J. "Role of sulfite additives in wine induced asthma: single dose and cumulative dose studies." 56, 2001, 763-769

[6] Vally, H.; Misso, N. L. A., Madan, V., "Clinical effects of sulphite additives." *Clinical and Experimental Allergy,* 39, 2009, 1643-1651.

[7] 27 C.F.R. § 4.321987

[8] Fazio, T.; Warner, C. R.; "A review of sulphites in foods: analytical methodology and reported findings." *Food Additives and Contaminants,* 7, 1990, 433-454. (And references cited therein.)

[9] Chen, L.; De Borba, B.; Rohrer, J.; "Determination of Total and Free Sulfite in Foods and Beverages." Thermo Fisher Scientific, 2016, 1-8.

[10] Scientific Equipment of Houston, Indicator to Detect Sulfite Quantofix 100 Analytical Strips, www.seohcorp.com/seoh-indicator-to-detect-sulfite-quantofix-100-analytical-strips/(accessed Sep. 23, 2017).

[11] Lavel Peelers, Titrets Sulfite Testing Kit, labelpeelers.com/equipment/testing/titrets-sulfite-testing-kit/?gclid-CjwKCAjwjJjOBRBVEiwAfvnvBFMTGlaMZtG52dxd5dRKfXbES9×3e38n7fEfM-UCn-BFNnlqvmrwBoCUzkQAvD_BwE (accessed Sep. 23, 2017).

[12] Monro, T. M.; Moore, R. L.; Nguyen, M. C.; Ebendorff-Heidepriem, H.; Skouroumounis, G. K.; Elsey, G. M.; Taylor, D. K.; "Sensing Free Sulfure Dioxide in Wine," *Sensors,* 12, 2012, 10759-10773.

[13] Chen, Q.; Yang, D.; Zhang, H.; Song, X.; Foley, J.; "Selective, Highly Sensitive Fluorescent Probe for the Detection of Sulfur Dioxide Derivatives in Aqueous and Biological Environments," *Analytical Chemistry,* 87, 2014, 609-616.

[14] Rossi, R. A.; Pierini, A. B.; Santiago, A. N.; "Aromatic substitution by the SRN1 reaction," *Oganic Reactions* 54, 1999, 1-271.

[15] Chahma, M.; Combellas, C.; Thiebault, A.; "Delocalized Nitrogen Carbanions in the SRN1 Reactions," *Journal of Oganic Chemistry,* 60, 1995, 8015-8022.

[16] Chahma, M.; Combellas, C.; Thiebault, A.; "Electrosynthesis of arylpyrroles and—indoles under SRN1 conditions," *Synthesis,* 4, 1994, 366-368.

[17] Kruse, C. G.; Bouw, J. P.; Can Hes, R.; Van de Kuilen, A.; Den Hartog, J. A. J.; "New methods for the synthesis of 2-arylpyrroles," *Heteroycles,* 26, 1987, 3141-3151.

[18] Seki, K.; Ohkura, K.; Terashima, M.; Kanaoka, Y.; "Photo-arylation. Part V. Photoreaction of 4-iodopyridine with heteroaromatics," *Heteroycles,* 24, 1986, 799-803.

[19] Firi, J.; "Heterocyclics by diene synthesis. Pyridylpyrroles from Diels-Alder adducts of nitroso compounds," *Chemische Berichte,* 101, 1968, 218-225.

[20] Overhoff, J.; "Preparation of the (4'-pyridyl)pyrroles." *Recueil des Travaux Chimiques des Pays-Bas et la Belgique,* 59, 1940, 741-744.

[21] Vysotskii, Y. B.; Zemskii, B. P.; Stupnikova, T. V.; Sagitullin, R. S.; "Quantum-chemical treatment of recyclization reactions. 5. Pyrrolylpyridines," *Khimiya Geterosiklicheskikh Soednenii,* 6, 1981, 799-782.

[22] Afonin, A. V.; Ushakov, I. A.; Sobenina, L. N.; Stepanova, Z. V.; Petrova, O. V.; Trofimov, B. A.; "Different types of hydrogen bonds in 2-substituted pyrroles and 1-vinylpyrroles as monitored by 1H, 13C and 15N NMR spectroscopy and ab initio calculations," *Magnetic Resonance in Chemistry,* 44, 2006, 59-65.

[23] Afonin, A.; Ushakov, I. A.; Simonenko, D. E.; Shmidt, E. Y.; Zorina, N. V.; Mikhaleva, A. I.; Trofimov, B. A.; "1H and 13C NMR Study of Bifurcated Intramolecular Hydrogen Bonds in 2,6-Bis(2-pyrrolyl)pyridine and 2,6-Bis(1-vinyl-2-pyrrolyl)pyridine," *Russian Journal of Organic Chemistry,* 41, 2005, 1516-1521.

[24] Noland, W. E.; Cole, K. P.; Britton, D.; "Five (1H-pyrrol-2-yl)pyridines," *Acta Crysallographica, Section C: Crystal Structure Communications,* C59, 2003, 263-267.

[25] Afonin, A.; Uskakov, I. A.; Petrova, O. V.; Sovenina, L. N.; Mikhaleva, A. I.; Voronov, V. K.; Trofimov, B. A.; "1H and 13C NMR study of the steric and electronic structure of 23-(pyridyl)pyrroles," *Russian Journal of Organic Chemistry,* 36, 2000, 1043-1049.

[26] Vega, I. E. D.; Gale, P. A.; Light, M. E.; Loeb, S. J.; "NH vs CH hydrogen bond formation in metal-organic anion receptors containing pyrrolylpyridine ligands," *Chemical Communications,* 39, 2005, 4913-4915.

[27] Mishra, S. J.; Gosh, S.; Stothert, A. R.; Dickey, C. A.; Blagg, B. S. J.; "Transfromation of the Non-Selective Aminocyclohexanol-Based Hsp90 Inhibitor into a Grp94-Selective Scaffold," *ACS Chemical Biology,* 12, 2017, 244-253.

[28] Iihama, T.; Hagiwara, K.; Maruge, S.; Sano, S.; Shimoda, S.; Horikoshi, Y.; "Preparation of pyrrole derivatives as agrochemical fungicides," JP 10324687 A 19981208, 1998.

[29] Federal Drug Administration, EPIPEN—epinephrine injection, www.accessdata.fda.gov/drugsatfda_docs/label/2012/019430s0531bl.pdf (accessed Sep. 23, 2017).

[30] Sarasota Anesthesia, Sulfite Containing Drugs, www.sarasotaanesthesia.com/pdf/Sulfite %20Containing %20Drugs.pdf (accessed Sep. 23, 2017).

[31] Thompson, J. B.; Toy, E.; "Determination of Sulfur Dioxide. Improved Monier-Williams Method," *Analytical Chemisty* 17, 1945, 612-615.

[32] Barbe, J. C.; de Revel, G.; Joyeux, A.; Lonvaund-Funel, A.; Betrand, A.; "Role of Carbonyl Compounds in $SO_2$ Binding Phenomena in Musts and Wines from Botrytized Grapes." *Journal of Agricultural and Food Chemistry,* 48, 2000, 3413-3419.

[33] Anzenbacher, P.; Jursikova, K.; Sessler, J. *J. Am. Chem. Soc.* 2000, 122, 9350.

[34] Beer, P. Cadman *J. Coord. Chem. Rev.* 2000, 205, 131.

[35] Beer, P. D.; Zheng, C.; Goulden, A. J.; Grieve, A.; Hesek, D.; Szemes, F.; Wear, T. *Chem. Comm.* 1994, 1269.

[36] Chang, K. C.; Sun, S. S.; Odago, M. O.; Lees, A. J. *Coord. Chem. Rev.* 2015, 284, 111.

[37] Chao, D.; Shitan, N. *J. Photochem. Photobiol, A* 2016, 1, 1.

[38] Chen, W.; Fang, Q.; Yang, D.; Hongyan, Z.; Song, X.; Foley, J. *Anal Chem.* 2015, 87, 609.

[39] Chen, W.; Liu, X.; Chen, S.; Song, X.; Kang, J. *RSC Adv.,* 2015, 5, 25409.

[40] Chen, Y.; Wang, X.; Yang, X.; Zhong, Y.; Li, Z.; Li, H. *Sensor. Actuator.,* 2015, 206, 268.

[41] Chen, Y.; Wang, X.; Yang, X.; Zhong, Y.; Li, Z.; Li, H. *Sensor. Actuator.,* 2015, 206, 268.

[42] Christianson, A. M.; Gabbai, F. *Chem. Comm.* 2017, 2471.

[43] Dadamos, T. R. L.; Teixeira, M. F. S. *Electrochim. Acta,* 2009, 54, 4552.

[44] Das, A.; Mondal, P.; Dasgupta, M.; Kishore, D.; Lahiri, G. K. *J. Chem. Soc. Dalton Trans.* 2016, 45, 2605.

[45] Devadas, B.; Sivakumar, M.; Chen, S. M.; Cheemalapati, S. *Electrochim. Acta,* 2015, 176, 350.

[46] Devaramani, S.; Malingappa, P. *Electrochim. Acta,* 2012, 85, 579.

[47] Dickson, S. J.; Patterson, M. J.; Willans, C. E.; Anderson, K. M.; Steed, J. W. *Chem. Eur. J* 2018, 24, 7296.

[48] Fermi, A.; Bergamini, G.; Roy, M.; Gingras, M.; Ceroni, P. *J. Am. Chem. Soc.* 2014, 136, 6395.

[49] Gale, P. A.; Busschaert, N.; Haynes, C. J. E.; Karagiannidis, L. E.; Kirby, I. L. *Chem. Soc. Rev.* 2014, 1, 205.

[50] Gaussian 16, Revision A. 03, Frisch, M. J.; Trucks, G. W.; Schlegel, H. B.; Scuseria, G. E.; Robb, M. A.; Cheeseman, J. R.; Scalmani, G.; Barone, V.; Petersson, G. A.; Nakatsuji, H.; Li, X.; Caricato, M.; Marenich, A. V.; Bloino, J.; Janesko, B. G.; Gomperts, R.; Mennucci, B.; Hratchian, H. P.; Ortiz, J. V.; Izmaylov, A. F.; Sonnenberg, J. L.; Williams-Young, D.; Ding, F.; Lipparini, F; Egidi, F.; Goings, J.; Peng, B.; Petrone, A.; Henderson, T.; Ranasinghe, D.; Zakrzewski, V. G.; Gao, J.; Rega, G. Zheng, W. Liang, M. Hada, M. Ehara, K. Toyota, R. Fukuda, N.; Hasegawa, J.; Ishida, M.; Nakajima, T.; Honda, Y.; Kitao, O.; Nakai, H.; Vreven, T.; Throssell, K.; Montgomery Jr., J. A.; Peralta, J. E.; Ogliaro, F.; Bearpark, M. J.; Heyd, J. J.; Brothers, E. N.; Kudin, K. N.; Staroverov, V. N.; Keith, T. A.; Kobayashi, R.; Normand, J.; Raghavachari, K.; Rendell, A. P.; Burant, J. C.; Iyengar, S. S.; Tomasi, J.; Cossi, M.; Millam, J. M.; Klene, M.; Adamo, C.; Cammi, R.; Ochterski, J. W.; Martin, R. L.; Morokuma, K.; Farkas, O.; Foresman, J. B.; Fox, D. J. Gaussian, Inc., Wallingford CT, 2016.

[51] Hargrove, A. E.; Nieto, S.; Zhang, T.; Sessler, J. L.; Anslyn, E. V. *Chem. Rev.* 2011, 111, 6603.

[52] He, Q.; Zhang Z.; Brewster, J. T.; Lynch, V. M.; Kim, S. K.; Sessler, J. L. *J. Am. Chem. Soc.* 2016, 31, 9779.

[53] Hidekazu, M.; Sessler, J. L. *Angew. Chem. Int. Ed.* 2001, 1, 154.

[54] Indumathy, R.; Perunninakulath, S. P.; Aiswarya, C. V.; Nair, B. U. *Polyhedron* 2014, 75, 22.

[55] Kaur, K.; Saini, R.; Kumar, A; Luxami, V.; Kaur, N.; Singh, P.; Kumar, S. *Coord Chem. Rev.* 2012, 17, 1992.

[56] Kim, S. K.; Sessler, J. L. *Chem. Soc. Rev.* 2010, 10, 3784.

[57] La, Y. K.; Hong J. A.; Jiyoun, L. *RSC Adv.* 2016, 6, 84098.
[58] Lee, K. S.; Kim, H. J.; Kim, G. H.; Shin, I.; Hong, J. I. *Org Let.* 2008, 10, 49.
[59] Levine, A. S.; Labuza, T. P.; Morley, J. E. *N. Engl J. Med.* 1985, 312, 628.
[60] Liu, A.; Ji, R.; Shen, S.; Cao, X.; Ge, Y. *New J. Chem.*, 2017, 41, 10096.
[61] Maduraiveeran, G.; Ramaraj, R. *Electrochem. Commun.*, 2007, 9, 2051.
[62] Maity, D.; Das, S.; Mardanya, S.; Baitalik, S. *Inorg. Chem.* 2013, 52, 6820.
[63] Montalti, M.; Prodi, L.; Zaccheroni N.; Charbonniere, L.; Douce, L.; Ziessel, R. *J. Am. Chem. Soc.* 2001, 123, 12694.
[64] Nikolantonaki, M.; Magiatis, P.; Waterhouse, A. *Anal Chem.* 2015, 87, 10799.
[65] Odago, M. O., Colabello, D. M., Lees, A. J. *Tetrahedron,* 2010, 66, 7465.
[66] Odago, M. O.; Colabello, D. M.; Lees, A. L. *Tetrahedron* 2010, 38, 7465.
[67] Odago, M. O.; Hoffman, A. E.; Carpenter, R. L.; Chi Tak Tse, D.; Sun, S. S.; Lees, A. J. *Inorg. Chimica. Acta.* 2011, 374, 558.
[68] Perrin, D. D.; Armarego, W. L. F.; Perri, D. R., Eds. *Purification of Laboratory Chemicals,* 2nd ed.; Pergamon Press: Oxford, U. K., 1980.
[69] Rawal, R.; Chawla, S.; Dahiya, T.; Pundir, C. S. *Anal Bioanal Chem.*, 2011, 401, 2599.
[70] Rommel, S.; Sorsche, D.; Dixit, A.; Rau, S. *Eur. J. Inorg. Chem.* 2016, 2016, 40.
[71] Roubinet, B.; Bailly, L.; Petit, E.; Renard, P.; Romieu, A. *Tetrahedron Lett.,* 2015, 56, 1015.
[72] Salimi, A.; Pourbeyram, S.; Amini, M. K. *Analyst,* 2002, 127, 1649.
[73] Schmitt, L. D.; Lees, A. J.; Selective Optical Aqueous Anion Detection, U.S. Patent Appl.; 62569193; Oct. 6, 2017.
[74] Spricigo, R.; Richter, C.; Leimkuehler, S.; Gorton, L.; Scheller, F. W.; Wollenberger, U. *Colloid. Surface A.,* 2010, 354, 314.
[75] Sun, S. S.; Lees, A. J. *Chem. Comm.* 2000, 1687.
[76] Sun, S. S.; Lees, A. J., Zavalij, P. Y. *Inorg. Chem.* 2003, 42, 3445.
[77] Sun, Y.; Zhong, C.; Gong, R.; Mu, H.; Fu, E. *J. Org Chem.*, 2009, 74, 7943.
[78] Tan L.; Lin W.; Zhu S.; Yuan L.; Zheng K. *Org. Biomol. Chem.*, 2014, 12, 4637.
[79] Tan, L.; Lin, W.; Zhu, S.; Yuan, L.; Zheng, K. *Org. Biomol. Chem.,* 2014, 12, 4637.
[80] Turkoglu, G.; Cinar, M. E.; Ozturk, T. *Eur. J. Org. Chem.* 2017, 31, 4552.
[81] Ulca, P.; Oeztuerk, Y.; Senyuva, H. *Z. Food Addit. Contam. Part B Surveill.* 2011, 4, 226.
[82] Wang, L.; Li, W.; Zhi, W.; Ye, D.; Wang, Y.; Ni, L.; Bao, X. *Dyes Pigments,* 2017, 147, 357.
[83] Wu, J. S.; Hwang, I. C.; Kim, K. S.; Kim, J. S. *Org Lett.* 2007, 9, 907.
[84] Wu, J.; Qu, Y.; Wang, L.; Huang, L.; Rui, Y.; Cao, J.; Xu, J. *Dyes Pigments,* 2017, 136, 175.
[85] Wu, M.; Li, K.; Li, C.; Hou, J.; Yu, X. *Chem. Comm.*, 2014, 183.
[86] Xu, G.; Wu, H.; Liu, X.; Feng, R.; Liu, Z. *Dyes Pigments,* 2015, 120, 322.
[87] Yang, W. H.; Purchase, E. C. R. *Can. Med. Assoc. J.* 1985, 9, 865, 880.
[88] Yang, X.; Yu, C.; Yexin L.; Zheng, L.; Lijun X.; Ning, Y.; Zheng L.; Lu, J.; Zhang, G.; Liu, C.; Zhang, G. *Spectrochim. Acta, Part A* 2015, 137, 1055.
[89] Yi, F. Y. Y.; Li, J. P.; Wu, D.; Sun, Z. M. *Chem. Eur. J* 2015, 21, 11475.
[90] Zhang, W.; Liu, T.; Huo, F.; Ning, P.; Meng, X.; Yin, C. *Anal Chem.,* 2017, 89, 8079.
[91] Zhao, D.; Cui, Y.; Yang, Y.; Qian, Y. *Cyst. Eng. Comm.* 2016, 21, 3746.
[92] Zhou, H.; Yang, W.; Sun, C. *Talanta,* 2008, 77, 366.

SUMMARY OF THE INVENTION

Sulfites are known allergens that cause difficulty breathing, skin rashes, and in extreme cases, death. There is no simple, accurate, and affordable test for sulfite in aqueous solution, and yet sulfites are present throughout food and wine consumer products. The present technology provides a selective, accurate, and simple assay for detection of sulfites in aqueous solutions with a lower limit of detection of 3.69 nM (0.000465 ppm, or 0.465 ppb). One implementation of the assay, with a practical limit of quantification of 0.84 ppm, is accurate to $\pm 8.0 \times 10^{-8}$ M (0.01 ppm).

The present technology thus provides an allergen (e.g., sulfite anion) test that is rapid, accurate, precise and is affordable. With this test, the knowledge of the concentration of sulfites in consumer products becomes now obtainable and represents vital new safety information.

The technology can be used in an analytical test (e.g., for the product manufacturer), or in the form of a sulfite test strip (e.g., targeted to consumers with sulfite sensitivities). The technology also has applications in environmental sciences. The test may also be used for pharmaceutical, chemical, and other industries. The technology provides parts per million sensitive sulfite detection in aqueous media, suitable for use in the food and wine industries, and in a user accessible allergen assay.

The assay presented here does not require the pretreatment of consumer product samples, nor does it require the use of hazardous reagents. It does not produce false positives as those tests that function via the ripper method (iodine titration), and is suitable for most sulfite-containing products. The test is rapid, affordable, and accurate within a large range of sulfite concentration, from as low as 10 ppm (demonstrated sensitivity as low as 0.8 ppm) to over 10,000 ppm, and has applications beyond the beverage industry. The test does not only sense sulfite, but functions as a sulfite capture method.

The procedure involves measuring the absorption spectrum with a spectrometer. In some cases, a two or three-point measurement may be made. The technique requires only simple math and simple analytical techniques that brewers, vintners, and food producers could follow from supplied literature in a kit, or any such assay timing, setup, calculations, etc. could be prompted or performed by an automated devices, such as a smartphone colorimeter with an appropriate app (downloadable software that executes within a smartphone environment, accessing the hardware and resources of the smartphone under control of the smartphone operating system).

The technology employs a simple aromatic heterocyclic system, the compound 4-(1H-pyrrol-2-yl)pyridine, which quickly, efficiently and selectively reacts with sulfite to produce a colorimetric change. The resulting interaction between the sulfite and the sensor molecule is a covalent bond that captures the sulfite. The reaction of 4-(1H-pyrrol-2-yl)pyridine and sulfite can also be used in nanoparticle synthesis. Its aromaticity and hetero-atoms provide a useful ligand for the design and synthesis of useful nanoparticles, e.g., fuel coils and drug delivery systems. The preferred sensor molecule according to the present technology,

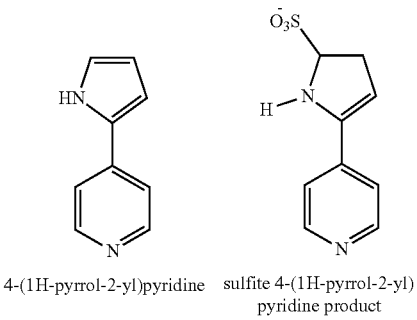

4-(1H-pyrrol-2-yl)pyridine    sulfite 4-(1H-pyrrol-2-yl) pyridine product has been synthesized using various techniques, and investigated in literature [14-28], for example as an herbicide [28]. A preferred synthetic route according to the present technology is disclosed in [18] and shown in FIG. 1 and can be monitored using UV-Visible spectroscopy as depicted in FIG. 2.

The product of the binding between sulfite and 4-(1H-pyrrol-2-yl)pyridine was isolated, as shown in FIG. 3, and examined using Nuclear Magnetic Resonance spectroscopy, as shown in FIG. 4. From the NMR data collected, it was concluded that interaction between sulfite and the sensor molecule was covalent in nature, and generally irreversible under ambient conditions. The product of 4-(1H-pyrrol-2-yl)pyridine and sulfite ion in an aqueous solvent is shown above.

The compound possesses a strong absorbance in the ultraviolet region of 289 nm, and a strong visible region of the spectrum at a wavelength of 463 nm, as shown in FIG. 5. Upon exposure to sulfite or bisulfite, the peak at 463 nm is bleached, as shown in FIG. 6. This bleaching occurs upon sequential addition of the sulfite/bisulfite until the maximum binding occurs.

The reaction may be monitored spectrometrically, and portable spectrometers are becoming increasingly popular and offer the possibility for onsite testing to occur. This not only benefits consumer product manufacturers but also environmental specialists that wish to do field testing for sulfite levels in water and soil. A spectrometer may be implemented using a modern cellphone camera, or as an add-on to a cellphone.

Zhang, C., Cheng, G., Edwards, P., Zhou, M. D., Zheng, S., & Liu, Z. (2016). G-Fresnel smartphone spectrometer. Lab on a Chip, 16(2), 246-250.

Hossain, M. A., Canning, J., Ast, S., Cook, K., Rutledge, P. J., & Jamalipour, A. (2015). Combined "dual" absorption and fluorescence smartphone spectrometers. Optics letters, 40(8), 1737-1740.

Wang, Yi, Xiaohu Liu, Peng Chen, Nhung Thi Tran, Jinling Zhang, Wei Sheng Chia, Souhir Boujday, and Bo Liedberg. "Smartphone spectrometer for colorimetric biosensing." Analyst 141, no. 11 (2016): 3233-3238.

Das, A. J., Wahi, A., Kothari, I., & Raskar, R. (2016). Ultra-portable, wireless smartphone spectrometer for rapid, non-destructive testing of fruit ripeness. Scientific reports, 6, 32504.

Kwon, H., Park, J., An, Y., Sim, J., & Park, S. (2014). A smartphone metabolomics platform and its application to the assessment of cisplatin-induced kidney toxicity. Analytica chimica acta, 845, 15-22.

Wang, L. J., Chang, Y. C., Sun, R., & Li, L. (2017). A multichannel smartphone optical biosensor for high-throughput point-of-care diagnostics. Biosensors and Bioelectronics, 87, 686-692.

Gallegos, Dustin, Kenneth D. Long, Hojeong Yu, Peter P. Clark, Yixiao Lin, Sherine George, Pabitra Nath, and Brian T. Cunningham. "Label-free biodetection using a smartphone." Lab on a Chip 13, no. 11 (2013): 2124-2132.

Yu, H., Tan, Y., & Cunningham, B. T. (2014). Smartphone fluorescence spectroscopy. Analytical chemistry, 86(17), 8805-8813.

Grasse, E. K., Torcasio, M. H., & Smith, A. W. (2015). Teaching UV-Vis Spectroscopy with a 3D-Printable Smartphone Spectrophotometer. J. of Chemical Education, 93(1), 146-151.

Hossain, M. A., Canning, J., Cook, K., Ast, S., Rutledge, P. J., & Jamalipour, A. (2015, July). Absorption and fluorescence spectroscopy on a smartphone. In Fifth Asia-Pacific Optical Sensors Conference. Proc. SPIE (Vol. 9655, pp. 96551Z-1).

Chang, B. Y. (2012). Smartphone-based chemistry instrumentation: digitization of colorimetric measurements. Bulletin of the Korean Chemical Society, 33(2), 549-552.

Dutta, S., Choudhury, A., & Nath, P. (2014). Evanescent wave coupled spectroscopic sensing using smartphone. IEEE Photonics Technology Letters, 26(6), 568-570.

Özdemir, G. K., Bayram, A., Kihç, V., Horzum, N., & Solmaz, M. E. (2017). Smartphone-based detection of dyes in water for environmental sustainability. Analytical Methods, 9(4), 579-585.

San Park, T., Li, W., McCracken, K. E., & Yoon, J. Y. (2013). Smartphone quantifies *Salmonella* from paper microfluidics. Lab on a Chip, 13(24), 4832-4840.

Mancuso, M., Cesarman, E., & Erickson, D. (2014). Detection of Kaposi's sarcoma associated herpesvirus nucleic acids using a smartphone accessory. Lab on a Chip, 14(19), 3809-3816.

Long, K. D., Yu, H. J., & Cunningham, B. T. (2015). 'Smartphone Spectroscopy: Three Unique Modalities for Point-Of-Care Testing. Next-Generation Spectroscopic Technologies VIII. Proc. Bellingham, WA: SPIE, 98227, 94820J.

Hossain, M. A., Canning, J., Ast, S., Rutledge, P. J., & Jamalipour, A. (2015). Early warning smartphone diagnostics for water security and analysis using real-time pH mapping. Photonic Sensors, 5(4), 289-297.

Li, Fenghua, Yu Bao, Dandan Wang, Wei Wang, and Li Niu. "Smartphones for sensing." Science bulletin 61, no. 3 (2016): 190-201.

See also, U.S. Pub. Patent Appln. and U.S. Pat. Nos. 20170270690; 20170238854; 20170231571; 20170224257; 20170198329; 20170184506; 20170183708; 20170173262; 20170166903; 20170102399; 20170099415; 20170079592; 20170022547; 20170020436; 20170000359; 20160374600; 20160327473; 20160319354; 20160291000; 20160289750; 20160283706; 20160273154; 20160263577; 20160239624; 20160167051; 20160161415; 20160117565; 20160080548; 20160076083; 20160038936; 20160025715; 20160008809; 20150359458; 20150310634; 20150293115; 20150293091; 20150291966; 20150247874; 20150247190; 20150244852; 20150227887; 20150116093;

20150091233; 20150055134; 20140356864; 20140335505; 20140329262; 20140315229; 20140286550; 20140248621; 20140214714; 20140211204; 20140206099; 20140120563; 20140081665; 20140065647; 20140057255; 20130309679; 20130280725; 20130156286; 20130080071; 9,731,391; 9,686,395; 9,619,627; 9,610,037; 9,569,858; 9,563,833; 9,557,331; 9,552,529; 9,549,703; 9,526,480; 9,526,450; 9,506,855; 9,476,159; 9,456,777; 9,445,749; 9,390,312; 9,241,663; 9,230,185; 9,228,953; 9,186,278; 9,149,806; 9,016,193; and 8,380,541.

An embodiment of the technology employs an automatically or manually-readable dipstick test. See, US 20160171690, 20150325006, 20150291628. According to this embodiment, 4-(1H-pyrrol-2-yl)pyridine is adsorbed onto or manufactured within a non-woven pad or porous surface. The pad or surface can be supported on various materials, such as thermoplastic, thermoset plastic, absorption pads, glass rods and paper strips etc. The preparation and use of such test systems are described in U.S. Pat. No. 6,406,862, 20100284858, and Y. Takahashi, H. Kasai, H. Nakashini, T. M. Suzuki, Angew. Chem. Int. Ed., 2006, 45, 913.

The 4-(1H-pyrrol-2-yl)pyridine indicator may be adsorbed on a top surface of an absorptive polyester pad, bound to one end of the dipstick, such that the end with the pad can be dipped into, and uniformly wet by, an aqueous analyte solution. In order to ensure quantitative reaction, the pad adsorbs a predetermined and repeatable volume of analyte. The 4-(1H-pyrrol-2-yl)pyridine indicator is maintained at or near the visible surface of the pad. The indicator may be encapsulated in a hydrogel, delayed release microcapsules or other material, so that the indicator is not lost in the analyte upon initial exposure, and only released until after the dipstick is removed from the analyte source. The hydrogel, microcapsules, or other encapsulating or delay material allow reaction of sulfite with the indicator to take place after the dipstick is removed from the aqueous analyte containing an unknown amount of sulfite, which then bleaches the indicator according to the amount of sulfite present. Since the quantity of indicator is fixed during manufacture, and the volume of analyte is determined by the characteristics of the pad, the color change is dependent on the concentration of sulfite in the analyte. The intensity of the indicator against the silica-alumina binder is then read. Since the pad or hydrogel adsorbs analyte at the surface, colored material in the analyte will not substantially interfere with reading of the color change at the surface.

A polymer hydrogel may be made, for example, of polyvinyl alcohol, acrylamide and glutaraldehyde. Hydrogels are polymeric networks consisting of crosslinked hydrophilic polymers that can absorb and retain a large amount of water within them. Polyacrylamide (PAM) has a typical three-dimensional (3D) network structure. PAM may be synthesized by a simultaneous crosslinking polymerization procedure using initiators like potassium peroxydisulphate.

An alternate type of sensor is a lateral flow sensor. In this case, the amount of fluid which reacts with the indicator is controlled, for example by providing a flow limited by fluid absorption of a pad. When the pad is saturated, flow ceases. Therefore, an indicator within the flow path can react with a predefined volume of analyte. The indicator may be maintained at the pad by encapsulation in a hydrogel, binding to a polymer, etc. See, Yetisen, Ali K., J. L. Martinez-Hurtado, Angel Garcia-Melendrez, Fernando da Cruz Vasconcellos, and Christopher R. Lowe. "A smartphone algorithm with inter-phone repeatability for the analysis of colorimetric tests." Sensors and Actuators B: Chemical 196 (2014): 156-160.

M. Webster, V. Kumar, Automated doctors: cell phones as diagnostic tools, Clin. Chem. 58 (2012) 1607-1609.

Z. J. Smith, K. Chu, A. R. Espenson, M. Rahimzadeh, A. Gryshuk, M. Molinaro, et al., Cell-phone-based platform for biomedical device development and education applications, PLoS ONE 6 (2011) e17150.

A. Coskun, J. Wong, D. Khodadadi, R. Nagi, A. Tey, A. Ozcan, A personalized food allergen testing platform on a cellphone, Lab Chip 13 (2012) 636-640.

H. Zhu, S. Mavandadi, A. F. Coskun, O. Yaglidere, A. Ozcan, Optofluidic fluorescent imaging cytometry on a cell phone, Anal. Chem. 83 (2011) 6641-6647.

A. W. Martinez, S. T. Phillips, G. M. Whitesides, Three-dimensional microfluidic devices fabricated in layered paper and tape, Proc. Natl. Acad. Sci. U.S.A 105 (2008) 19606-19611.

S. Wang, X. Zhao, I. Khimji, R. Akbas, W. Qiu, D. Edwards, et al., Integration of cell phone imaging with microchip ELISA to detect ovarian cancer HE4 biomarker in urine at the point-of-care, Lab Chip 11 (2011) 3411-3418.

N. R. Pollock, J. P. Rolland, S. Kumar, P. D. Beattie, S. Jain, F. Noubary, et al., A paper-based multiplexed transaminase test for low-cost, point-of-care liver function testing, Sci. Transl. Med. 4 (2012) 152ra29.

O. Mudanyali, S. Dimitrov, U. Sikora, S. Padmanabhan, I. Navruz, A. Ozcan, Integrated rapid-diagnostic-test reader platform on a cellphone, Lab Chip 12 (2012) 2678-2686.

L. Shen, J. A. Hagen, I. Papautsky, Point-of-care colorimetric detection with a smartphone, Lab Chip 12 (2012) 4240-4243.

H. Zhu, S. O. Isikman, O. Mudanyali, A. Greenbaum, A. Ozcan, Optical imaging techniques for point-of-care diagnostics, Lab Chip 13 (2013) 51-67.

R. W. Hunt, Measuring Colour, 3rd ed., Fountain Press, England, 1998.

T. Smith, J. Guild, The C.I.E. colorimetric standards and their use, Trans. Opt. Soc. 33 (1931) 73-134.

A. W. Martinez, S. T. Phillips, M. J. Butte, G. M. Whitesides, Patterned paper as a platform for inexpensive, low-volume, portable bioassays, Angew. Chem. Int. Ed. 46 (2007) 1318-1320.

P. Yager, T. Edwards, E. Fu, K. Helton, K. Nelson, M. R. Tam, et al., Microfluidic diagnostic technologies for global public health, Nature 442 (2006) 412-418.

C. D. Chin, T. Laksanasopin, Y. K. Cheung, D. Steinmiller, V. Linder, H. Parsa, et al., Microfluidics-based diagnostics of infectious diseases in the developing world, Nat. Med. 17 (2011) 1015-1019.

Cate, David M., Jaclyn A. Adkins, Jaruwan Mettakoonpitak, and Charles S. Henry. "Recent developments in paper-based microfluidic devices." Analytical chemistry 87, no. 1 (2014): 19-41.

Meredith, Nathan A., Casey Quinn, David M. Cate, Thomas H. Reilly, John Volckens, and Charles S. Henry. "based analytical devices for environmental analysis." Analyst 141, no. 6 (2016): 1874-1887.

Yamada, Kentaro, Hiroyuki Shibata, Koji Suzuki, and Daniel Citterio. "Toward practical application of paper-based microfluidics for medical diagnostics: state-of-the-art and challenges." Lab on a Chip 17, no. 7 (2017): 1206-1249.

Yetisen, Ali K., Haider Butt, Lisa R. Volpatti, Ida Pavlichenko, Matjaz Humar, Sheldon J J Kwok, Heebeom Koo et al. "Photonic hydrogel sensors." Biotechnology advances 34, no. 3 (2016): 250-271.

Yetisen, Ali K., Yunuen Montelongo, Malik M. Qasim, Haider Butt, Timothy D. Wilkinson, Michael J. Monteiro, and Seok Hyun Yun. "Photonic nanosensor for colorimetric detection of metal ions." Analytical chemistry 87, no. 10 (2015): 5101-5108.

Christodouleas, Dionysios C., Alex Nemiroski, Ashok A. Kumar, and George M. Whitesides. "Broadly available imaging devices enable high-quality low-cost photometry." Analytical chemistry 87, no. 18 (2015): 9170-9178.

Wang, ShuQi, Thiruppathiraja Chinnasamy, Mark A. Lifson, Fatih Inci, and Utkan Demirci. "Flexible substrate-based devices for point-of-care diagnostics." Trends in biotechnology 34, no. 11 (2016): 909-921.

Moonrungsee, Nuntaporn, Somkid Pencharee, and Jaroon Jakmunee. "Colorimetric analyzer based on mobile phone camera for determination of available phosphorus in soil." Talanta 136 (2015): 204-209.

Masawat, Prinya, Antony Harfield, and Anan Namwong. "An iPhone-based digital image colorimeter for detecting tetracycline in milk." Food chemistry 184 (2015): 23-29.

Gabriel, Ellen F M, Paulo T. Garcia, Thiago M G Cardoso, Flavio M. Lopes, Felipe T. Martins, and Wendell K T Coltro. "Highly sensitive colorimetric detection of glucose and uric acid in biological fluids using chitosan-modified paper microfluidic devices." Analyst 141, no. 15 (2016): 4749-4756.

McCracken, Katherine E., Scott V. Angus, Kelly A. Reynolds, and Jeong-Yeol Yoon. "Multimodal imaging and lighting bias correction for improved PAD-based water quality monitoring via smartphones." Scientific reports 6 (2016): 27529.

Kangas, Michael J., Raychelle M. Burks, Jordyn Atwater, Rachel M. Lukowicz, Pat Williams, and Andrea E. Holmes. "Colorimetric sensor arrays for the detection and identification of chemical weapons and explosives." Critical reviews in analytical chemistry 47, no. 2 (2017): 138-153.

U.S. Pub. Patent Application Nos. and U.S. Pat. Nos. 8,901,366; 8,642,355; 8,623,292; 8,574,919; 8,475,731; 8,470,609; 8,383,047; 8,003,399; 7,846,383; 7,674,615; 7,504,235; 7,282,349; 7,280,201; 7,229,783; 7,087,397; 6,818,180; 5,962,215; 20180106524; 20170219576; 20170087549; 20150126947; 20140273270; 20140271362; 20140147931; 20140057362; 20130295690; 20130196053; 20120042722; 20100311181; 20100290948; 20100226822; 20090305395; 20090181416; 20090157024; 20090157023; 20090068061; 20090033727; 20080145945; 20080102473; 20080057528; 20080003141; 20070286771; 20070048816; 20070048815; 20070048182; 20060292040; 20060275920; 20060132786; 20060115580; 20060008847; 20050223983; 20050130253; 20040127883; 20040028608; 20030175153; 20030116257; 20030067516; 20030007039; 20020101486; 20020085069; and 20010039057.

If strongly colored aqueous analyte does interfere with reading, a set of control pads with predefined color gradation on the corresponding silica alumina coated pads may be provided, which are also immersed into the analyte, to thereby color the control pads in the same way as the active indicator pad, and thus normalize the reading.

Alternately, the pad may include a non-interfering oxidizer, such as chlorate or nitrite, to degrade organic colorants while the reaction of sulfite with the indicator is occurring. Similarly, if the colorants are lipophilic, lipid phase absorptive material may be provided to decolorize the solution.

The nature of the product presents a further option. While the colored indicator is not highly charged, the bleached indicator is highly charged, and therefore can engage in an exchange reaction on an ion exchange resin. If the resin is loaded with a second dye, which is more weakly bound to the resin than the sulfite reaction product of the indicator, then the reaction will cause both a decrease in the absorption of the indicator (e.g., at 463 nm), while concurrently causing an increase in absorption at an absorption wavelength of the second dye.

Similarly, the increase in the sulfite reaction product of the indicator may be detected with an ion-sensitive field effect transistor (ISFET), metal-oxide-silicon (MOS) senor, voltametric sensor, other secondary sensor. The rationale is that, while specifically and sensitively detecting the sulfite is difficult, the reaction product is a charged organic sulfite, which can be directly detected in differentways. Further, since the amount of the reaction product increases quantitatively with the amount of sulfite consumed, the assay is less sensitive to the initial concentration of indicator. Further, measuring the reaction product is not inconsistent with measuring the bleaching of indicator, and therefore a double-measurement technology is available.

Therefore, the technology is not limited to a spectrometric measurement of bleaching of the 4-(1H-pyrrol-2-yl)pyridine indicator dissolved in diluted aqueous analyte media, and rather the bleaching (loss of absorption at a defined wavelength, which itself may be a pH compensated wavelength) may be detected in various phases, and/or the increase in reaction product measured. However, as discussed below, the spectrometric assay in aqueous phase has been tested, and shown to be accurate, sensitive, immune to interference, simple and inexpensive to conduct.

The bleaching of 4-(1H-pyrrol-2-yl)pyridine by reaction with sulfite was investigated, and it was determined that the practical lower limit of quantification (PLQ) was 0.84 ppm Q 0.01 ppm. The PLQ is defined as a 10% loss in the signal intensity at a wavelength of 463 nm. The lower limit of detection, LOD, was determined to be 3.69 nM.

A competitive study was done to establish selectivity and rule out the possibility of false positives ansing from other common anions. The sensor was mixed with a known amount of an anion. The absorbance was measured, and then sulfite added, and the absorbance measured again. This test was repeated for fluoride, chloride, bromide, iodide, nitrate, nitrite, sulfate, bisulfate, carbonate, and bicarbonate. For all cases, no bleaching of the peak at 463 nm occurred unless sulfite or bisulfite were present. It is important to note that when carbonate and bicarbonate were added, a red shift in the absorbance occurred. This is believed to be a result of the sensor compound becoming ionized due to the anion's basicity. Therefore, a pH correction of the absorbance value at 463 nm might alleviate the need for a full spectrum evaluation.

Even still, upon addition of sulfite to the solutions containing the sensor and carbonate (or bicarbonate), a bleaching effect did occur. This indicates that the absorbance of the sensor molecule is unaffected by other anions, and the reduction in the absorbance for sulfite is unaffected by the other anions. This confirms that the sulfites chemosensor is selective.

The test was also done in various solvents. Solvent systems that were water, mixed water-organic, or organic acids were bleached upon addition of sodium sulfite. A solution (8 mL) of $3.47 \times 10^{-4}$ M 4-(1H-pyrrol-2-yl)pyridine was prepared using pure deionized water as the solvent. Into a vial, 1 mL of the solution was added. Then 1 mL of a second solvent was added, such that a 50/50 solvent ratio was achieved, and the resulting solution was well mixed. Next, 0.2 mL of a 1 M aqueous solution of sodium sulfite was added to the vial. The vial was shaken, and observed for color changes. This was repeated 8 times using various solvents, see Table 1 below. All solutions except the 50/50 water/acetone showed a loss of color after the addition of sulfites.

TABLE 1

| Vial | Solvents (%) | Response |
| --- | --- | --- |
| 1 | Water (100) | Bleaching |
| 2 | Water (50)/DMSO (50) | Partial Bleaching |
| 3 | Water (50)/THF (50) | Partial Bleaching |
| 4 | Water (50)/Ethanol (50) | Bleaching |
| 5 | Water (50)/Methanol (50) | Bleaching |
| 6 | Water (50)/DMF (50) | Bleaching |
| 7 | Water (50)/Acetone (50) | No Response |
| 8 | Water (50)/Acetonitrile (50) | Bleaching |

Table 1 shows a summary of the results of using a mixed solvent system as the environment for the 4-(1H-pyrrol-2-yl)pyridine-sulfite interaction. Sensing occurred in 50/50 mixtures of aqueous-organic solvent mixtures for all solvents tested except for acetone. This is believed to be caused by a competing interaction between acetone and water in which the little acid present is consumed by the solvent rather than 4-(1H-pyrrol-2-yl)pyridine. Acidic conditions are required for an interaction between the sensor molecule and sulfite to occur.

To study the effects of pH on the system, 4-(1H-pyrrol-2-yl)pyridine was dissolved in buffers at various pHs (2-10) and the absorbance measured. Above pH 8, the absorbance underwent a significant red shift; due to the system being ionized. At all pH values, there was a significant amount of bleaching in the absorbance, as shown in Table 2. The experiments represented in FIGS. 3, 4, 5, 6, and 7 allowed the mechanism to be established as an acid catalyzed addition of sulfite to the sensor molecule, and confirmed the pathway proposed in FIG. 3.

An experiment to determine whether the system binds free or total sulfites was conducted. An aqueous solution of $1.10 \times 10^{-4}$ M solution of 4-(1H-pyrrol-2-yl)pyridine was prepared. Additionally, a pH 4 buffer solution containing 0.1M sodium sulfite, and 0.1M pyruvic acid (pyruvic acid is a component in many consumer products, including wines and ciders, that will bind sulfite) so that all the sulfite was bound by pyruvic acid was also prepared. 100 µL of the buffer solution containing the bound sulfites were injected into a 1.00 cm path length quartz cuvette, using a micro syringe, containing the sensor solution. Upon addition of the bound sulfite solution to the sensor, no bleaching was observed, and it was concluded that the sensor only detects unbound (free) sulfite/bisulfite.

This technology is applicable in the fields of chemistry, and several consumer products including: wine, cider, beer, baked goods, soup mixes, jams, canned vegetables, pickled foods, sauerkraut, gravies, dried fruit, potato chips, trail mix, vegetable juices, sparkling fruit juices, pasteurized fruit juices, unpasteurized fruit juices, tea, condiments, molasses, fresh or frozen shrimp, guacamole, maraschino cherries, pectin, and dehydrated, pre-cut, or peeled potatoes. Sulfites are also added to medications to prevent browning; in this case the technology is also applicable, one such example being injectable epinephrine [29]. Others include: sulfacetamide sodium, dexamethasone, prednisolone acetate, prednisolone, isuprel hydrochloride, isoetharine, hydrocortisone (injectable), amikacin, metaraminol, betamethasone phosphate, prochlorperazine, dexamethasone phosphate, meperidine, dopamine, gentamycin, isoetharine hydrochloric acid, isoproterenol (injectable), norepinephrine, tobramycin, procaine, promethazine, chlorpromazine, and lidocaine with epinephrine [30].

Using a simple, accurate, and selective chemosensor according to the present technology would eliminate waste, testing time, and, most importantly, risk to the labs conducting this test, on top of providing the key information needed by the companies using sulfites as a preservative.

The test presented here does not require the pretreatment of consumer product samples, nor does it require the use of hazardous reagents. It does not produce false positives as those tests that function via the ripper method, and is suitable for most sulfite-containing products.

The test is rapid, affordable, and accurate within a large range of sulfite concentration, from as low as 0.84 ppm to over 10,000 ppm, and has applications beyond the beverage industry.

While it does require the use of a spectrometer, portable options are becoming increasingly popular and offer the possibility for onsite testing to occur. This not only benefits consumer product manufacturers, but also environmental specialists that wish to do field testing for sulfites levels in water and soil.

It is therefore an object to provide a method of determining a free sulfite concentration in an aqueous analyte, comprising: adding the aqueous analyte to compound having a 4-(1H-pyrrol-2-yl)pyridine ligand structure, e.g., 4-(1H-pyrrol-2-yl)pyridine itself, and measuring a bleaching of an absorbance in an optical spectrum of 4-(1H-pyrrol-2-yl)pyridine resulting from reaction with free sulfite in the analyte, after a period of time. A practical lower limit of quantification may be 0.84 ppm. Dilution of the analyte allows an arbitrary upper limit.

It is another object to provide an apparatus for determining a concentration of sulfite in an aqueous analyte, comprising: a spectrometer; and a calculation device, configured to determine and output a concentration of sulfite in the aqueous analyte based on a bleaching of 4-(1H-pyrrol-2-yl) pyridine determined by the spectrometer. The spectrometer may comprise a spectrophotometer which measures optical absorption at 463 nm. The apparatus may further comprise at least one of a pH sensor and a pH adjuster, wherein the determination of the concentration of sulfite is pH compensated. The apparatus may be configured to provide a practical lower limit of quantification of 0.84 ppm.

Another object provides a method of determining a free sulfite concentration in an aqueous analyte, comprising: providing 4-(1H-pyrrol-2-yl)pyridine; adding a first amount of the aqueous analyte to the 4-(1H-pyrrol-2-yl)pyridine, and measuring a first bleaching of an optical absorption of the 4-(1H-pyrrol-2-yl)pyridine; adding a second amount of the aqueous analyte to the 4-(1H-pyrrol-2-yl)pyridine after the first bleaching, and measuring a second bleaching of an optical absorption of the 4-(1H-pyrrol-2-yl)pyridine; and calculating the free sulfite concentration in the aqueous analyte based on at least the second bleaching.

The compound having a 4-(1H-pyrrol-2-yl)pyridine ligand structure may be immobilized on a solid support and/or bound to a polymer. It may also be encapsulated, or provided in a slow release (erodible) polymer form.

The compound having a 4-(1H-pyrrol-2-yl)pyridine ligand structure may be 4-(1H-pyrrol-2-yl)pyridine, having an optical absorption; and said reacting may comprise adding an aqueous analyte containing a concentration of sulfite to the compound; further comprising measuring a bleaching of the optical absorption by free sulfite in the aqueous analyte.

The optical absorption is measured at an absorption peak, e.g., 463 nm, of an absorption spectrum of the e.g., 4-(1H-pyrrol-2-yl)pyridine. Measurements may also be taken off the absorption peak, and as a spectrogram. The measuring may comprise determining an absorption spectrum within an optical wavelength range.

The aqueous analyte may be selected from the group consisting of a food, a wine, a juice, a beer, a cider, a chemical solution, an environmental sample, and a pharmaceutical product.

The aqueous analyte and/or solution in which the 4-(1H-pyrrol-2-yl)pyridine reacts may have a pH of between 2 and 10.

The method may further comprise calculating an amount and/or concentration of free sulfite in the aqueous analyte. Alternately, the method may determine whether the aqueous analyte has greater than or less than a predetermined amount or concentration of sulfite.

The calculation of the amount of free sulfite in the aqueous analyte may be pH-compensated, or a pH titration may occur. A buffer may be used to modify the pH to within an acceptable range.

The aqueous analyte may be added to the compound in a quantity sufficient to bleach the 4-(1H-pyrrol-2-yl)pyridine by 10% at 463 nm, or other diminution at 463 nm or another wavelength of measurement. For example, the absorption may also be measured at 400, 410, 420, 430, 440, 441, 442, 443, 444, 445, 446, 447, 448, 449, 450, 451, 452, 453, 454, 455, 456, 457, 458, 459, 460, 461, 462, 464, 465, 466, 467, 468, 469, 470, 471, 472, 473, 474, 475, or 480 nm. The target reduction in absorption may be, e.g., 5%, 7.5%, 10%, 15%, 20%, 30%, 40%, 50%, 60%, 70%, 80%, 90%, 95%, 97.5%, 98%, 98.5%, 99%, or 99.5%.

The compound may be provided as an aqueous solution of 0.022 M 4-(1H-pyrrol-2-yl)pyridine.

The measuring may comprise determining an absorption spectra within a visible light range. The measurement may optionally extend into the ultraviolet and/or infrared spectrum.

The solution with the analyte may have a pH of between 2 and 10. The measurement of the bleaching of the absorbance peak of the optical spectrum of the solution with the analyte may be pH compensated. The pH may be measured electrochemically, or using a pH indicator dye which is not reactive with either the 4-(1H-pyrrol-2-yl)pyridine solution or the sulfite, and which produces optical changes at wavelengths different from the 4-(1H-pyrrol-2-yl)pyridine bleaching. As a result, the pH may be determined by the same spectrometer as the sulfite, and in the same sensing medium.

It is also an object to provide an apparatus for determining a concentration of sulfite in an aqueous analyte, comprising: a spectrophotometer; an aqueous solution of 4-(1H-pyrrol-2-yl)pyridine; and a calculation device, configured to determine a concentration of aqueous analyte based on a bleaching of the aqueous solution of 4-(1H-pyrrol-2-yl)pyridine by addition of the aqueous analyte. The calculating device may be further configured to pH compensate the bleaching.

The apparatus may further comprise a pH titrator configured to normalize a pH of the aqueous solution of 4-(1H-pyrrol-2-yl)pyridine mixed with the aqueous analyte. The apparatus may further comprise a pH buffer which neutralizes or normalizes a pH of the analyte solution, without altering free sulfite concentration or interaction with the 4-(1H-pyrrol-2-yl)pyridine solution. For example, a phosphate buffer or ion exchange resin may be used to ensure that the solution is at a known pH.

The apparatus may further comprise a fluidic device configured to add the aqueous analyte in a sufficient quantity to bleach the aqueous solution of 4-(1H-pyrrol-2-yl)pyridine by 10% at 463 nm.

It is a further object to provide a method of determining a free sulfite concentration in an aqueous analyte, comprising: providing an aqueous solution of 4-(1H-pyrrol-2-yl)pyridine; initially adding a first amount of the aqueous analyte to the aqueous solution, and measuring a first bleaching of an absorbance peak of an optical spectrum of the 4-(1H-pyrrol-2-yl)pyridine by free sulfite; subsequently adding a second amount of the aqueous analyte to the aqueous solution, and measuring a second bleaching of an absorbance peak of an optical spectrum of the 4-(1H-pyrrol-2-yl)pyridine by free sulfite; and calculating the free sulfite concentration based on at least the second bleaching. The second bleaching may, for example achieve a cumulative bleaching of ten percent. Alternate endpoints may be 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95%, 96%, 97.5%, 98%, 98.5%, or 99%. As shown in FIG. 11, the decrease in signal is asymptotic at 85%, while the decrease is approximately linear with increasing sulfite up to $5 \times 10^{-5}$ M sulfite.

The bleaching is preferably measured at 463 nm, but the peak may be pH sensitive, and therefore may be measured at a different wavelength. The wavelength may be selected based on pH, temperature, or other parameter. Likewise, the wavelength may also be selected based on the existence of potentially interfering substances.

As discussed above, an optical measurement may be analyzed together with a non-optical measurement, such as an electrochemical measurement of the indicator-sulfite reaction product. It is noted that, even in cases where indicator is consumed other than by reaction with sulfite or bisulfite, the reaction product of the indicator may differ, leading to a means to distinguish a competing reaction. A ratiometric (e.g., two-point measurement) may be employed.

The device may be a smartphone, or the optical sensor and calculating components of the device may be those of a smartphone, with additional components provided.

The capabilities of 4-(1H-pyrrol-2-yl)pyridine have been investigated by adding a non-aqueous sulfite solution to an aqueous solution of 4-(1H-pyrrol-2-yl)pyridine. After the addition of the sulfite to the solution, bleaching occurred. 4-(1H-pyrrol-2-yl)pyridine can also be used as a sulfite sensor in mixed organic-aqueous solvent systems. Upon the addition of sulfite to these mixed solvent solutions containing the sensor molecule, bleaching occurred.

The product between 4-(1H-pyrrol-2-yl)pyridine and sulfite is susceptible to chemical changes that could be used to back calculate the concentration of sulfites in a given sample. The reaction product may have unique optical properties that can also be measured. The composition appears generally colorless in the visible spectrum, but may have discernable features in infrared and/or ultraviolet, or NMR.

A method is therefore provided consisting of providing 4-(1H-pyrrol-2-yl)pyridine, adding an analyte containing sulfite, and optically reading a reduction in the 4-(1H-pyrrol-2-yl)pyridine by a loss of absorption at e.g., 463 nm. Advantageously, a light emitting diode (LED) or laser diode may be used to generate light at about 463 nm. The illuminator may be hand-held and/or battery operated. The illuminator may be a narrow-band illuminator, such as a 463 nm blue laser diode or 450-470 nm blue LED, or a broadband illuminator such as a white LED (e.g., blue LED plus yellow phosphor, e.g., cerium-doped yttrium aluminum garnet ($Ce^{3+}$:YAG)). The illuminator may scan a range of emitted wavelengths, for example by allowing the LED or laser diode to heat during a use cycle, or by use of a filter.

An organic LED (oLED) sensor may also be employed

The system may include a fluidic or microfluidic system to accurately dispense quantities of reagents, and thus allow precise quantitative measurements.

The system may also operate by titration of sulfite, in which the indicator concentration is diminished to near zero by consumption by sulfite. In this case, an instrument seeks to reduce the optical absorption of a known quantity of the indicator to zero, by successive addition of the analyte. Therefore, a differential sensor in which the optical path is successively switched between a volume containing the indicator and an identical one which does not, and so is compensated for absorption by the analyte.

A hand held autotitrator-visible spectrometer 2-in-1 may be used to automatically perform the detection, using a solution of 4-(1H-pyrrol-2-yl)pyridine and the sulfite analyte, which are is automatically mixed together, and a color change is detected.

Because of the sensitivity of the lower limit of detection, e.g., a PLQ of 0.84 ppm, the amount of analyte added to a solution of indicator may be small. This avoids dilution error of the indicator, and also dilutes the effect of any colored interfering substances in the analyte.

While measurement at a single wavelength, e.g., 463, is possible, another embodiment of the invention performs spectroscopy in a range including, but not limited to, NMR, IR, UV-vis, and visible spectroscopy to measure the interaction between sulfite and 4-(1H-pyrrol-2-yl)pyridine.

Another embodiment of the invention employs cyclic voltammetry to measure the reaction between sulfite and 4-(1H-pyrrol-2-yl)pyridine. This is a non-optical method, and therefore may be performed in addition to the optical method(s), to provide additional data.

Because the indicator forms a stable adduct with sulfite, it may be immobilized in a filter to remove free sulfite from a liquid medium. For example, the 4-(1H-pyrrol-2-yl)pyridine may be immobilized to a polysaccharide or cellulosic matrix, bound within a cross-linked hydrogel, covalently bonded to a polyvinyl alcohol, polyacrylonitrile, polyester, chitosan, or other acidic, neutral, or basic polymers.

The 4-(1H-pyrrol-2-yl)pyridine may be bound to an anion exchange resin in an ion exchange column, to determine the amount of sulfites in an analyte.

A further embodiment provides a solution of 4-(1H-pyrrol-2-yl)pyridine in titret form, to which the analyte is added, and change in color measured with a detector or naked eye. See, www.midwestsupplies.com/media/pdf-printouts/how_do_i_use a_titret_kit.pdf. The detector must have a PLQ of 0.84 ppm.

A still further method employs 4-(1H-pyrrol-2-yl)pyridine provided on a dipstick or other "lab on paper" form, that either gives a general concentration of sulfite in a sample or a dipstick that has a positive result above a certain amount of sulfites, or provides an indication of sulfite concentration.

A method is also provided for using solid (tablet or pellet) 4-(1H-pyrrol-2-yl)pyridine form, dropped in a small amount of liquid analyte, to give a colored solution when the concentration of sulfites is below a certain level and/or a colorless solution when the concentration of sulfites is above a certain level. The product formed by reaction of sulfite and 4-(1H-pyrrol-2-yl)pyridine may be used as a means of quantifying the free sulfite concentration. The product may be subsequently altered, for example by extraction by use of an exchange or affinity medium, and modification after release from the medium, for example, the sulfite reaction product may be a substrate for sulfite oxidase EC 1.8.3.1, Baeyer-Villiger monooxygenases, or various bacterial enzymes. The product may also be reduced, to form a sulfide (thiol or sulfhydryl) as shown in FIG. 12. The enzymatic products could then be measured, in some cases electrochemically. The result, for example, could return the colored 4-(1H-pyrrol-2-yl)pyridine, or a 4-(1H-pyrrol-2-yl)pyridine sulfate, or other modified indicator, as a means of measuring the free sulfite concentration.

While the preferred indicator is 4-(1H-pyrrol-2-yl)pyridine, other derivatives may also be suitable. For example, while the 1-, 2- and 3-position should remain unblocked, and occupied by H or only labile substituents, other hydrogens may be substituted with substituted or unsubstituted alkane, alkene, heteroalkane, heteroalkene, cyclically bridged, cyclic substituents, halogen substituents, etc. For example, a methyl may occupy the 4-position. Similarly, the pyridine may also be substituted, so long as the transition state of the reaction with sulfite has a sufficiently low activation energy, and the reaction is not sterically hindered. Thus, the invention also encompasses a method using derivatives or closely related compounds of 4-(1H-pyrrol-2-yl)pyridine, that have a similar interaction with sulfite.

DETAILED DESCRIPTION OF THE PREFERRED EMBODIMENT

While anion sensors have made significant advances, relatively few selective, naked eye, water-soluble sensors exist.

4-(1H-pyrrol-2-yl)pyridine, is a novel anion sensor which displays a substantial color loss upon addition of sodium sulfite in pure water (and other aqueous solvents). A variety of anions were tested for their effect on bleaching, including: halides, phosphates, sulfates, and hydroxide, but all solutions remained unchanged aside from the sulfite which displayed bleaching. To understand this selective interaction further, the sensor and the mechanism through which it senses were studied using UV-vis, IR, and 1H NMR experiments. The sensor was determined to have a ten percent decrease in the lowest absorption band upon the addition of $10^{-7}$ M sodium sulfite. This result was found to be an irreversible acid-catalyzed nucleophilic addition to the C4 position of the pyrrole. Similar results have been found to occur between pyrrole and sodium bisulfite, but none with sulfite and under the same ambient conditions, and certainly not with a color loss. (See, Treibs, A., Leibigs. Ann. Chem. 1963, 664, 140-145.). In addition to its capabilities as a sensor, the molecule is simple to make, and is synthesized using photochemical methodologies and requires little purification.

Figure 1:
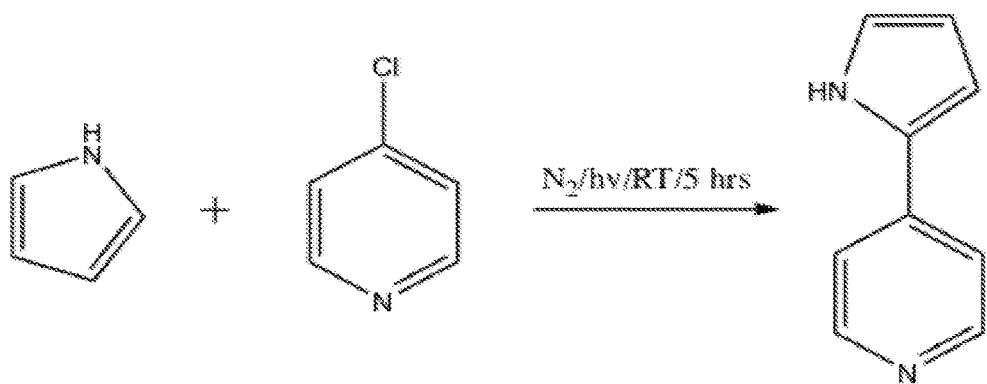
FIG. 1 shows the synthetic pathway used to prepare 4-(1H-pyrrol-2-yl)pyridine.
Figure 2:
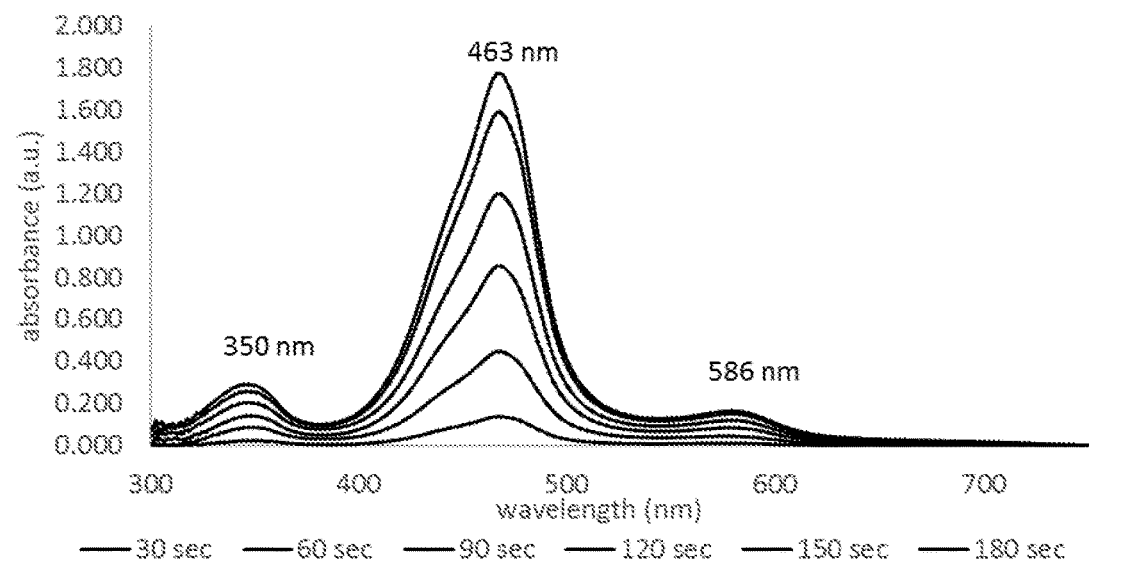
FIG. 2 shows a change in the optical absorption spectrum over time during the irradiation and photochemical synthesis of 4-(1H-pyrrol-2-yl)pyridine.

FIG. 1 shows the synthetic pathway used to prepare 4-(1H-pyrrol-2-yl)pyridine. A solution of freshly distilled pyrrole, 4-chloropyridine, and dried dichloromethane was mixed and purged with nitrogen gas for one hour. The colorless solution was then irradiated for 5 hours with ultraviolet light (hv) at room temperature. The resulting mixture was a dark green. FIG. 2 shows the changes in the absorption spectrum over time during the photochemical synthesis and irradiation of 4-(1H-pyrrol-2-yl)pyridine. The product was purified using extraction and the yellow compound concentrated to dryness to afford a yield of approximately 64%. The product was investigated using Nuclear Magnetic Resonance (NMR) and UV-vis spectroscopy.

In more detail, synthesis of 4-(1H-pyrrol-2-yl)pyridine was conducted using a modified photochemical synthesis first described by Seki, Ohkura, Terashima, and Kanoaka [18]. 0.150 g (0.001 moles) of 4-chloropyridine were added to 100 mL of dried dichloromethane in a 250 mL round bottom flask. 0.967 mL of pyrrole were then added to the solution. The entire reaction mixture was then purged with $N_2$ gas. The mixture was then irradiated for 5 hours at 293K using a medium pressure Oriel Mercury/Xenon arc lamp without filtration. The reaction was extracted with 10% hydrobromic acid in a separatory funnel. The aqueous layers were collected, combined, and neutralized with sodium carbonate. This solution was then extracted a second time with dried dichloromethane before being concentrated to dryness to afford a yellow powder with a yield of 0.0923 g (64.02%). 1H NMR (600 MHz, CDCl3): δ8.46 (2H, d, J=6 Hz), δ7.73 (1H, s, NH), δ7.28 (2H, d, J=6 Hz), δ6.57 (1H, d, J=6 Hz), δ6.06 (1H, d, J=6 Hz), δ6.02 (1H, m, J=6 Hz).

Figure 3:
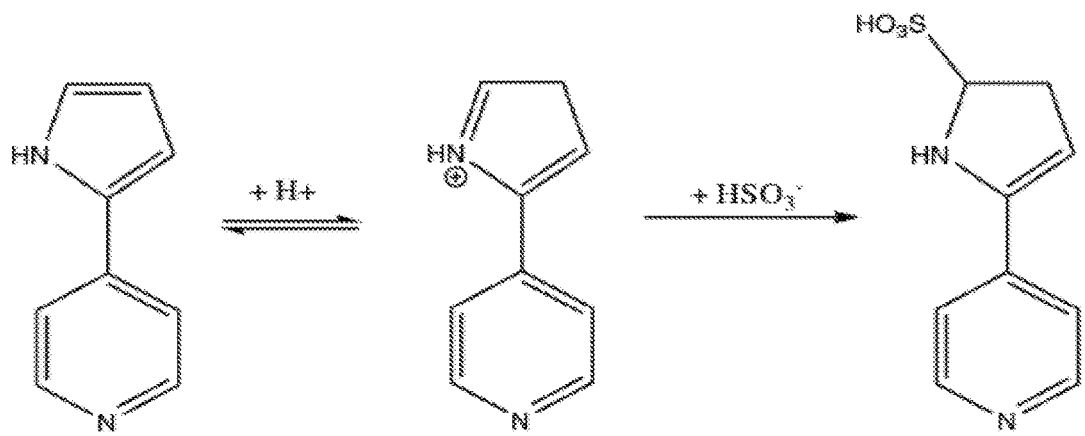
FIG. 3 shows the interaction of 4-(1H-pyrrol-2-yl)pyridine with sulfite following an acid catalyzed addition reaction between the anion and the sensor molecule.

FIG. 3 shows the interaction of 4-(1H-pyrrol-2-yl)pyridine with sulfite following an acid catalyzed addition reaction between the anion and the sensor molecule. It was determined that the interaction was irreversible, indicating a stable covalent bond between sulfite and the sensor molecule. To test the response of the sensor, to a small amount of an aqueous solution of 4-(1H-pyrrol-2-yl)pyridine (0.022 M), 0.7 mL of 0.1 M sodium sulfite was added. A dramatic bleaching of the yellow solution occurred. This bleaching was found to be irreversible and determined to be the formation of a covalent bond between sulfite and 4-(1H-pyrrol-2-yl)pyridine.

Figure 4:
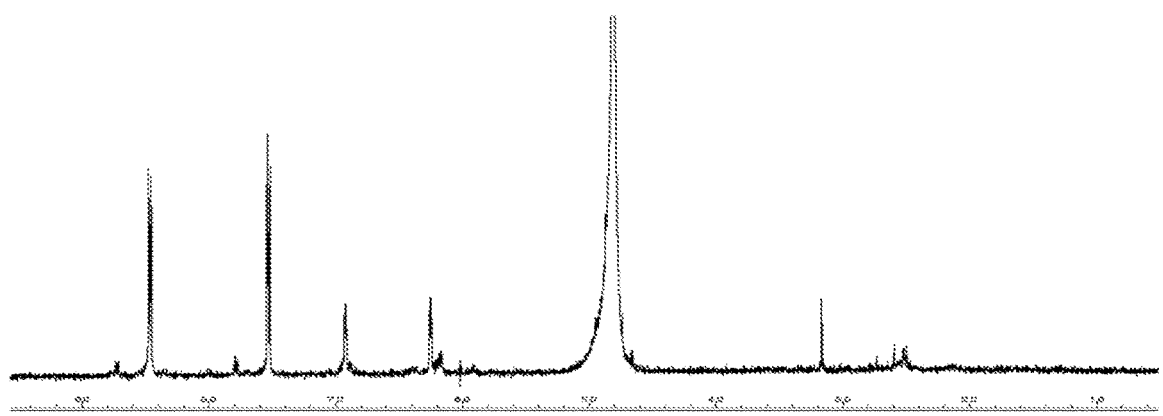
FIG. 4 shows an NMR spectrum of the sulfite 4-(1H-pyrrol-2-yl)pyridine product.

FIG. 4 shows an NMR spectrum of the sulfite 4-(1H-pyrrol-2-yl)pyridine product, indicating the formation of a bond between the anion and the sensor molecule. The triplets at δ6.94 and δ6.25, as well as the peaks at δ3.18 and δ2.59, show a strong correlation to the predicted spectra for the covalently bonded product, confirming the interaction from FIG. 3. Isolation of the 4-(1H-pyrrol-2-yl)pyridine/sulfite compound was done. The isolated compound was dissolved in 0.5 mL of deuterated water and placed in a 535 pp high frequency glass NMR tube for analysis by a 600 MHz Brucker NMR, FIG. 4. A clear change in multiplicity occurred as well as the growth of peaks in the aliphatic rejoin. 1H NMR (600 MHz, D$_2$O): δ8.47 (2H, d, J=6 Hz), δ7.54 (2H, d, J=6 Hz), δ6.93 (2H, d, J=6 Hz), δ6.25 (1H, d, J=6 Hz), δ3.18 (1H, d, J=6 Hz), δ2.59 (1H, m, J=6 Hz);

All UV-vis spectra were taken on an Aligent 8453 UV-vis spectrophotometer, with a 1.00-cm path length quartz cuvette, over the wavelengths of 250 nm to 700 nm. All NMR data was collected on a 600 MHz Brucker NMR using 535 pp high frequency glass tubes. All experiments were done at room temperature, 293 K. The instrument was referenced with 3.00 mL of deionized water and then an absorbance spectrum of 4-(1H-pyrrol-2-yl)pyridine was taken using 3.00 mL of a 0.022 M aqueous solution.

Figure 5:
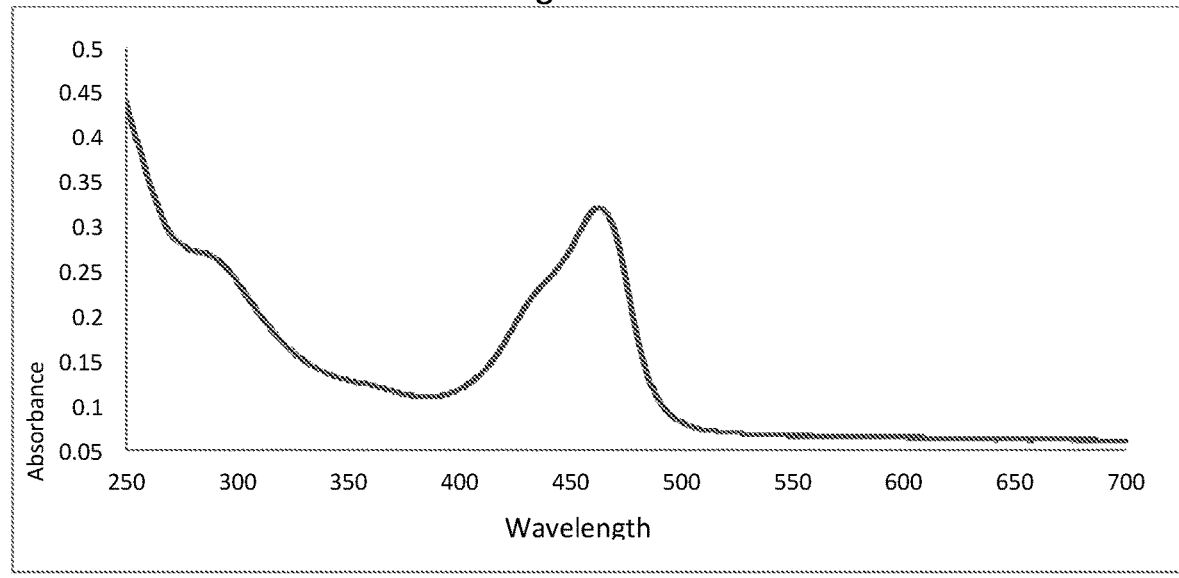
FIG. 5 shows a plot of absorbance versus wavelength of light for 4-(1H-pyrrol-2-yl)pyridine.

FIG. 5 shows a plot of absorbance versus wavelength of light for 4-(1H-pyrrol-2-yl)pyridine. The absorbance was scanned from 250 nm to 700 nm and the solution was measured in a 1.00-cm path length quartz cuvette on an Aligent 8453 instrument. Two peaks were observed, one at 289 nm and one at 463 nm. The peak at 463 nm gives rise to the compound's characteristic yellow color.

Figure 6:
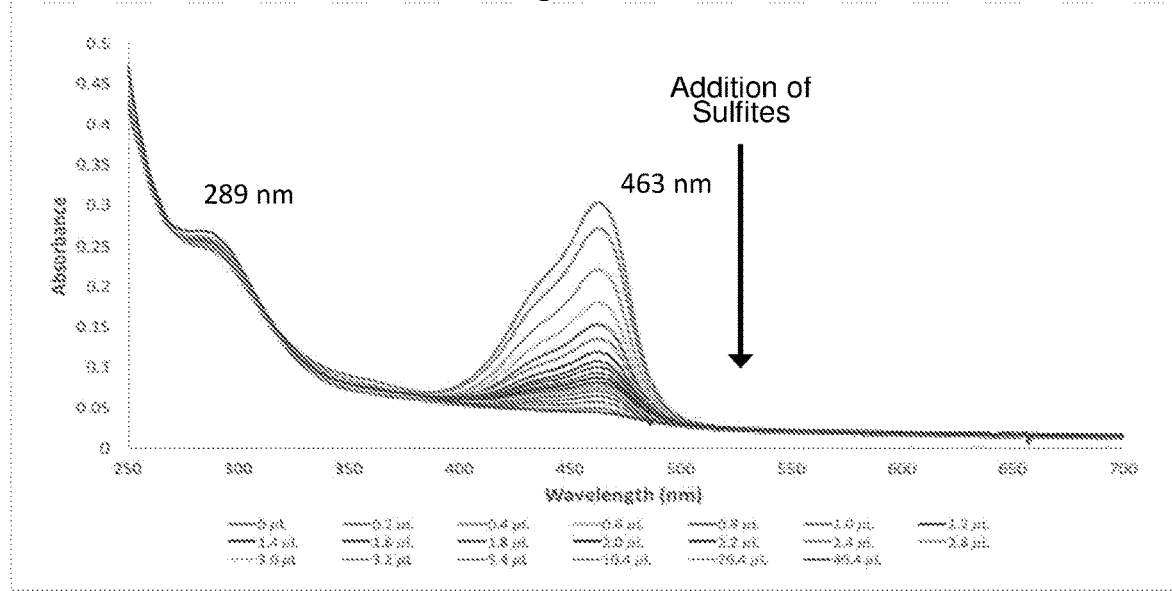
FIG. 6 shows a titration plot of absorbance versus wavelength of light of 4-(1H-pyrrol-2-yl)pyridine in a 1.00-cm path length quartz cuvette.

A UV-vis titration was done, using the 0.022 M solution of 4-(1H-pyrrol-2-yl)pyridine and the 0.1 M sodium sulfite solution. The instrument was referenced with deionized water, and then the absorbance spectrum of the solution of 4-(1H-pyrrol-2-yl)pyridine was measured. To 3.00 mL of the 4-(1H-pyrrol-2-yl)pyridine solution, 0.20 µL of the sulfite solution was injected using a micro syringe. The mixture was shaken, and the absorbance read. A 10% decrease in the peak intensity at 463 nm was observed, as shown in FIG. 6. This step was repeated until no further reduction in the peak at 463 nm was achieved. This corresponds to a 74% reduction of the peak intensity, as shown in FIG. 6.

FIG. 6 shows a plot of absorbance versus wavelength of light of 4-(1H-pyrrol-2-yl)pyridine in a 1.00-cm path length quartz cuvette on an Aligent 8453 instrument. Initially, no sulfite is added, and the absorbance spectrum was recorded. Then a small amount, typically 0.2 µL of a concentrated (0.1 M) sodium sulfite solution is added stepwise. (The total volumes of 0.1 M sodium sulfite are shown above) Each time the sulfite solution is added a new absorption spectrum is recorded. With each addition of sulfite, the peak at 463 nm is gradually bleached until no further reduction in the peak intensity is observed and the solution is optically colorless. This occurs after adding 40.4 µL of the sulfite solution.

An absorption titration was performed, using a 0.022 M aqueous solution of 4-(1H-pyrrol-2-yl)pyridine and a 0.1 M sodium sulfite solution. To 3.00 mL of the 4-(1H-pyrrol-2-yl)pyridine solution, 0.20 L (0.84 ppm) of the sulfite solution was added. A 10% decrease in the peak intensity at 463 nm was observed, as well as an isosbestic point at 312 nm. Additions of sulfite were repeated until no further reduction in the peak at 463 nm was achieved, 40.4 μL. This corresponds to 74% reduction of the peak intensity. These changes in absorbance were only observed for sodium sulfite and sodium bisulfite, revealing the sensor molecule's selectivity.

The Limit of Detection (LOD) was determined by standard methods (3a/m) and found to be 3.69 nM. The practical lower of quantification (PLQ) was established, via injecting 0.20 μL of 0.1 M sodium sulfite to a 0.022 M aqueous solution of 4-(1H-pyrrol-2-yl)pyridine and a loss in 10% of the peak intensity was achieved. This was repeated ten times and resulted in an average loss of 9.79% (N=10), or the detection of 0.80 ppm±0.01 ppm sodium sulfite.

Figure 7:
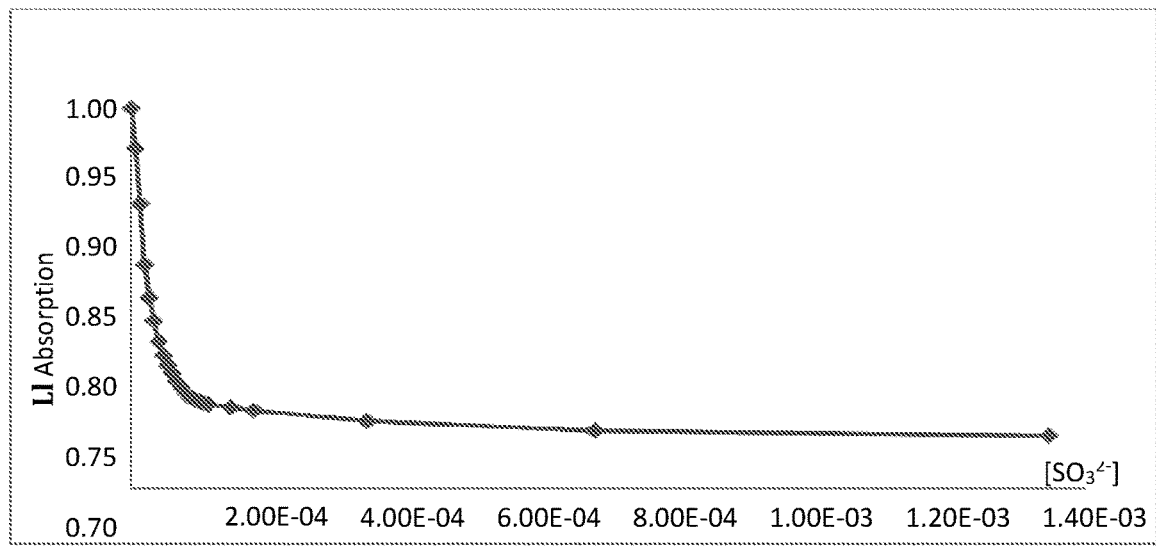
FIG. 7 shows a change in absorbance signal of the sensor molecule upon addition of sulfite.

FIG. 7 shows a change in absorbance signal of the sensor molecule upon addition of sulfite. The data is taken from FIG. 6 and is then plotted to determine the amount that the signal is reduced by as a result of adding sulfite. A 10% reduction in the signal intensity occurs after adding as little as 0.2 μL ($6.67 \times 10^{-6}$ M) sulfite. A loss of 74% of the signal intensity is observed after adding 40.4 μL ($1.35 \times 10^{-3}$ M) sulfite.

Figure 8:
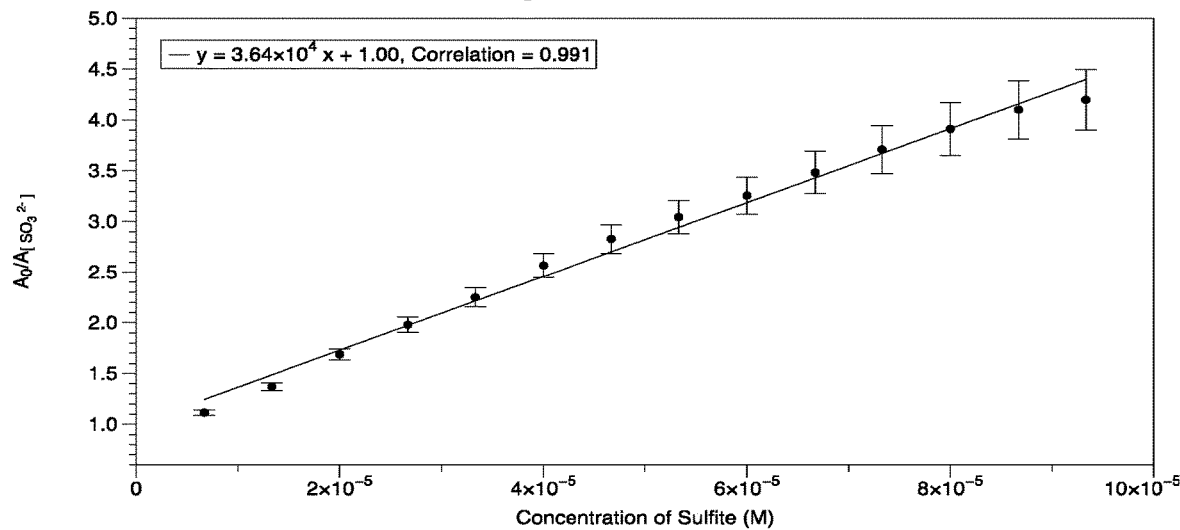
FIG. 8 shows a calibration plot of the linear region of the absorbance ratio (initial absorbance/absorbance after sulfites are added, at 463 nm) versus concentration of sulfite.

It was determined that the test is linear within $6.67 \times 10^{-6}$ M-$9.33 \times 10^{-5}$ M ($R^2 = 0.991$). A calibration curve was developed from the change in the absorbance after sulfite is added, as shown in FIG. 8.

Figure 9:
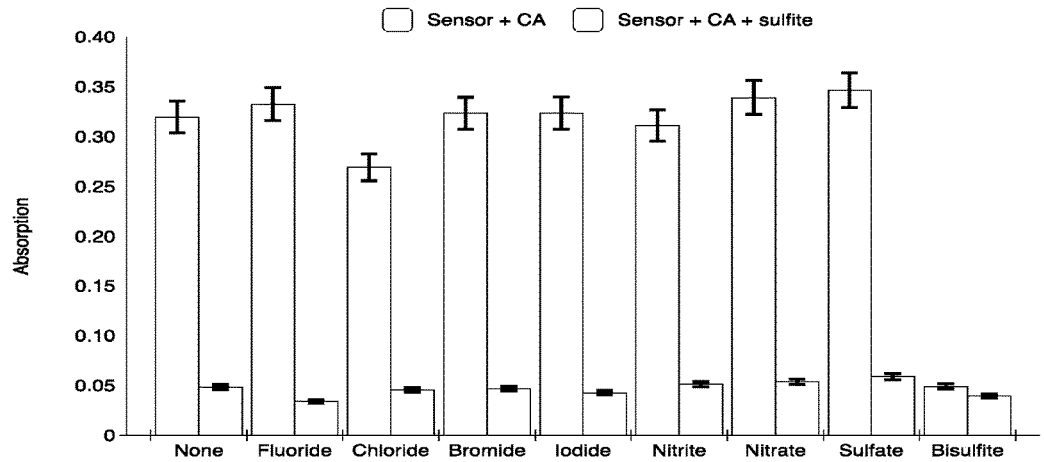
FIG. 9 shows absorption data (also error bars) of the sensor molecule with 20 equivalents of various common anions added (black). To these solutions 1.5 equivalents of sulfite was added and dramatic bleaching occurred (white).

A competitive study was carried out on 4-(1H-pyrrol-2-yl)pyridine to rule out the possibility of false positives and confirm selectivity. An aqueous solution of (0.022 M) 4-(1H-pyrrol-2-yl)pyridine was made and its absorbance spectrum recorded. To this, 20 equivalents of a common anion (fluoride, chloride, bromide, iodide, nitrate, nitrite, sulfate, bisulfate, bisulfite) was added and the absorbance of the resulting solution taken (see FIG. 9). Then 5.50 μL of a concentrated (0.62 M) solution of sodium sulfite was added and the resulting absorbance taken. In all cases, except that of sulfite and bisulfite, no bleaching was observed with any other anion, (see FIG. 9); the absorbance remained unchanged, despite addition of the anion solution. Carbonate and bicarbonate were also tested, and a substantial red shift of the absorbance occurred; this is due to the system being ionized by the anions. Additionally, no loss in color was observed, until the sulfite was added. This emphasizes the molecule's specificity and selectivity for sulfite/bisulfite over any other anion tested.

Table 2 shows the absorbance of an aqueous solution of 0.022 M 4-(1H-pyrrol-2-yl)pyridine at 463 nm and at various pHs before and after adding sulfite. Within a range of pH 2 to pH 8 approximately 96% of the signal is lost upon adding sulfite. pHs 9 and 10 had significant red shifts in their peaks because the 4-(1H-pyrrol-2-yl)pyridine was ionized. At higher pHs, the net reduction in the peak intensity after adding sulfite is near 58%. Above pH 8, the sensor is less effective and less sensitive, although a reduction in the peak intensity is still achieved. These buffers were adjusted for pH with hydrochloric acid or sodium hydroxide. The solutions at pH 9 and 10 had the same red shifted absorbance as observed in the competitive study with carbonate/bicarbonate. The absorbance of the buffered solutions was recorded. To the solutions, a concentrated solution of sodium sulfite was added. The resulting solution's absorbance was recorded. Between the ranges of pH 2-8, approximately 96% of the signal is bleached. Above pH 8, only about 58% of the signal is bleached, suggesting the compound being ionized.

From this result, it was determined that the reaction was pH dependent, thus strongly suggesting acid-catalyzed addition reaction as the mechanism.

Sulfites (sulfite and bisulfite) are preservatives added to products to prevent browning and spoilage. They react with various ingredients within the products they preserve, including acetaldehyde, acetoin, α-ketoglutaric acid, pyruvic acid, methylglyoxal, hydrated acetaldehyde, hemiacetal, hydrated ketoglutaric acid, L-xylosone, 5-keto-D-fructose, galacturonic acid, hydrated pyruvic acid, and hydrated methylglyoxal. Once reacted, the sulfite is considered "bound." Meanwhile, an adequate concentration of unbound or "free" sulfite must remain in the product in order to preserve it.

To test differences in response to free and bound sulfite, like those found in wine and other fermented products. A pH 4 buffer solution of 0.1 M pyruvic acid and 0.1 M sodium sulfite was made. Pyruvic acid has been found to strongly bind sulfites in wine and other fermented products. [32] An aqueous $1.56 \times 10^4$ M solution of 4-(1H-pyrrol-2-yl)pyridine was made and the absorbance recorded. To this, 200 μL of the bound sulfite solution was added. The resulting absorbance was measured. No change in the absorbance was detected, thus proving that the sensor molecule only detects unbound (free) sulfites.

TABLE 2

| Experiment | $A_0$ | $A_1$ | % decrease in signal |
|---|---|---|---|
| pH 2 | 0.385 | 0.014 | 96.357 |
| pH 3 | 0.383 | 0.013 | 96.577 |
| pH 4 | 0.359 | 0.010 | 97.143 |
| pH 5 | 0.388 | 0.033 | 91.551 |
| pH 6 | 0.373 | 0.014 | 96.291 |
| pH 7 | 0.321 | 0.012 | 96.261 |
| pH 8 | 0.302 | 0.009 | 96.969 |
| | | Average | 95.878 |
| pH 9 | 0.167 | 0.079 | 52.580 |
| pH 10 | 0.121 | 0.047 | 60.943 |
| | | Average | 56.761 |

Table 3 is a conversion table relating the volume of consumer product added to achieve a 10% reduction in the peak intensity at 463 nm to the concentration of free sulfites in the consumer product. The table is designed to work with 3.00 mL of a 0.038 M solution of 4-(1H-pyrrol-2-yl)pyridine, whose absorbance is near 1.000, and the volumes of consumer product added will not significantly dilute the solution. A competitive study was done on 4-(1H-pyrrol-2-yl)pyridine to rule out the possibility of false positives and confirm selectivity. An aqueous solution of (0.022 M) 4-(1H-pyrrol-2-yl)pyridine was made and its absorbance spectrum recorded. To this, 5.50 μL of 0.44 M solutions of common anions (fluoride, chloride, bromide, iodide, nitrate, nitrite, sulfate, bisulfate, bisulfite, carbonate, and bicarbonate) were mixed with 4-(1H-pyrrol-2-yl)pyridine and the absorbance of the resulting solution taken. In all cases except bisulfite, carbonate, and bicarbonate, the absorbance once the anion solution was added remained unchanged. In the case of bisulfite, the solution was bleached. For the carbonate and bicarbonate solutions, a substantial red shift of the absorbance occurred; this is because of the system being ionized by the anions. Additionally, no loss in color was observed. Then a concentrated (0.44 M) solution of sodium sulfite was added and the resulting absorbance taken. In all cases, the absorbance became bleached by the addition of sodium sulfite, demonstrating the solution's selectivity for only sulfites, and does not give false positives.

TABLE 3

| Volume of Consumer Product Added (μL)* to Achieve 10% Reduction in Absorbance at 463 nm | Concentration of Sulfite (ppm) |
|---|---|
| 1 | 2520.0 |
| 2 | 1260.0 |
| 3 | 840.0 |
| 4 | 630.0 |
| 5 | 504.0 |
| 6 | 420.0 |
| 7 | 360.0 |
| 8 | 315.0 |
| 9 | 280.0 |
| 10 | 252.0 |
| 11 | 229.1 |
| 12 | 210.0 |
| 13 | 193.8 |
| 14 | 180.0 |
| 15 | 168.0 |
| 16 | 157.5 |
| 17 | 148.2 |
| 18 | 140.0 |
| 19 | 132.6 |
| 20 | 126.0 |
| 21 | 120.0 |
| 22 | 114.5 |
| 23 | 109.6 |
| 24 | 105.0 |
| 25 | 100.8 |
| 33 | 76.4 |
| 50 | 50.4 |
| 101 | 25.0 |
| 168 | 15.0 |
| 252 | 10.0 |

*volumes added in μL will not incur a dilution effect on addition to a 3.00 mL solution of 0.038M of 4-pyrrolylpyridine.

Figure 10:
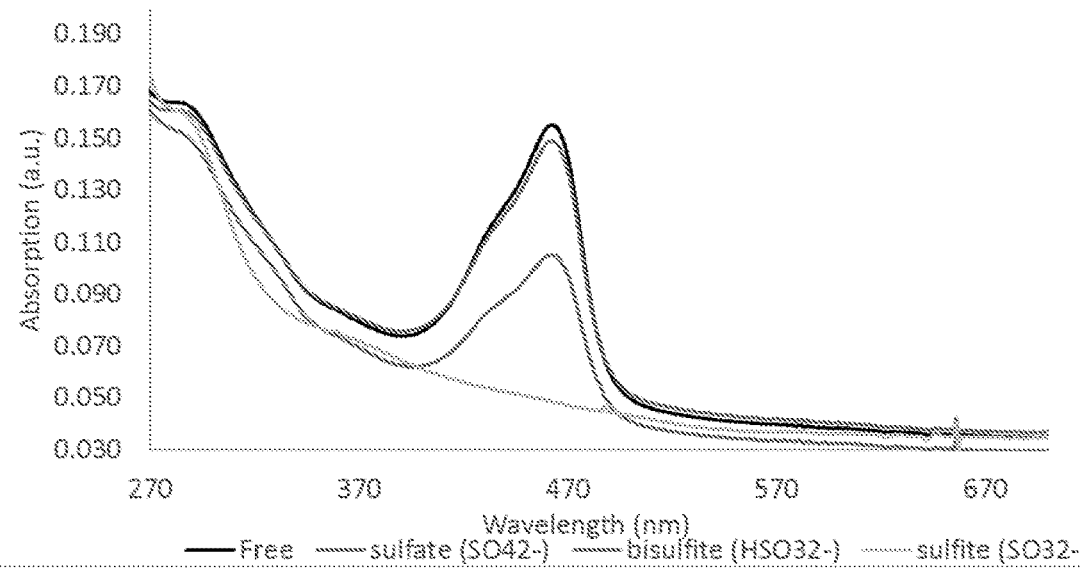
FIG. 10 shows the difference in optical absorption of the optical absorption spectrum of 4-(1H-pyrrol-2-yl)pyridine when interacting with different anions, including sulfate, sulfite and bisulfite.
Figure 11:
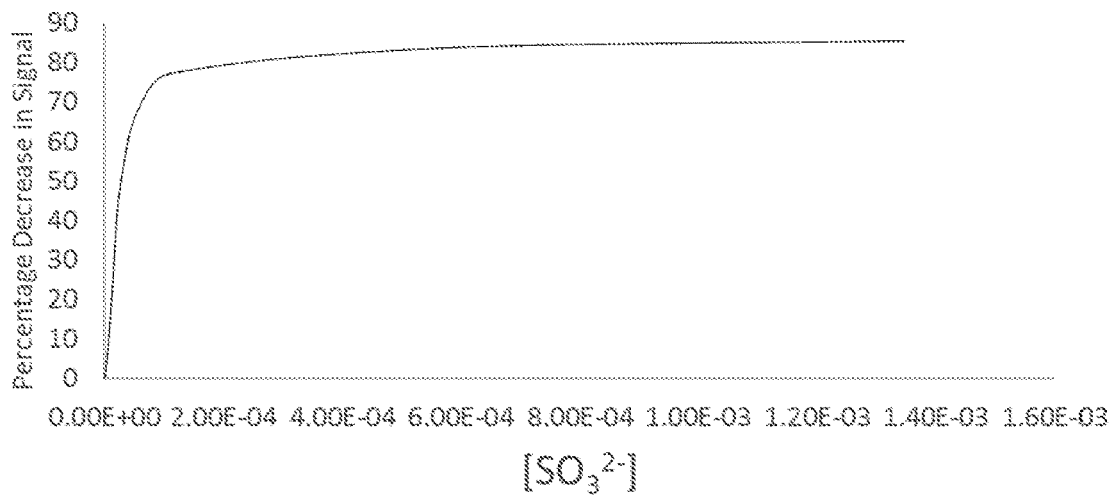
FIG. 11 shows the percentage decrease in signal vs. concentration of sulfite of 4-(1H-pyrrol-2-yl)pyridine at 463 nm.
Figure 12:
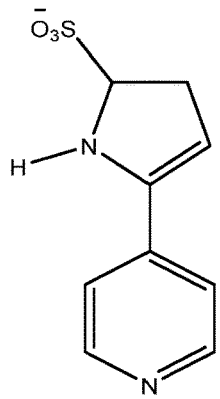
FIG. 12 shows a reaction pathway for reduction of the sulfite group to a thiol or sulfhydryl, of the reaction product of 4-(1H-pyrrol-2-yl)pyridine and sulfite.
Figure 12:
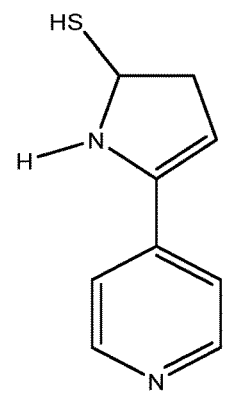

4-(1H-pyrrol-2-yl)pyridine was also tested against ascorbic acid (from Women's One A Day® ($3.41 \times 10^{-4}$ M)) and citric acid (lemon juice $5.01 \times 10^{-5}$ M) for the possibility of them interfering with the test. When no sulfite was added, no bleaching occurred. After the addition of sulfites (sulfite and bisulfite), bleaching occurred. As shown in FIG. 10, sulfate does not substantially interfere.

Various white, red, rose and sparkling wines as well as two hard ciders were tested for their sulfite concentration by 4-(1-H-pyrrol-2-yl)pyridine. To solutions of the sensor, microliter aliquots were added until a 10% loss at 463 nm was observed. Sulfite concentrations were found to be within the range of 28.38 ppm to 10.78 ppm (see table 4).

TABLE 4

Concentration of sulfite in various wines

| Type | Average Volume to 10% Decrease (μL, N = 3) | Concentration of Sulfite (M) | Concentration of Sulfite (ppm) |
|---|---|---|---|
| Pinot Grigio | 49.92 | $1.83 \times 10^{-4}$ | 23.11 |
| Moscato | 51.75 | $1.77 \times 10^{-4}$ | 22.29 |
| White Zinfadel | 66.60 | $1.37 \times 10^{-4}$ | 17.32 |
| Red Moscato | 107.00 | $8.55 \times 10^{-5}$ | 10.78 |
| Brut Champagne | 40.65 | $2.25 \times 10^{-4}$ | 28.38 |
| Cider (Dry) | 779.38 | $1.17 \times 10^{-5}$ | 1.48 |
| Cider (Semi Dry) | 784.73 | $1.16 \times 10^{-5}$ | 1.47 |

Example

Prepare a 0.038 M aqueous solution of 4-pyrrolylpyridine. Quantitatively transfer 3.00 mL to a 1.00-cm path-length cuvette and record the spectrum; the absorbance should be near 1.00 absorbance units. Using a micro syringe, begin injecting the consumer product to be tested, and record the spectrum. Once a 10% decrease in the absorbance has been achieved, use Table 2, or the equation below, to determine the concentration of sulfite in the consumer product. The product may need to be injected several times depending on the concentration. [Sulfites]-2520/V, Where, V, corresponds to the volume, in microliters, of consumer product added to 3.00 mL of a 0.038 M solution of 4-(1H-pyrrol-2-yl)pyridine to achieve a 10% reduction in the absorbance intensity.

What is claimed is:

1. A method of detecting a free sulfite in an aqueous analyte, comprising:
   reacting a first amount of the free sulfite in the aqueous analyte, with a compound having a 4-(1H-pyrrol-2-yl)pyridine ligand structure to perform a first bleaching;
   measuring a first optical absorption corresponding to the first bleaching of the compound having the 4-(1H-pyrrol-2-yl)pyridine;
   adding a second amount of the free sulfite in the aqueous analyte with the compound having the 4-(1H-pyrrol-2-yl)pyridine after the first bleaching, to perform a second bleaching;
   measuring a second optical absorption corresponding to the second bleaching of the 4-(1H-pyrrol-2-yl)pyridine; and
   calculating the free sulfite concentration in the aqueous analyte based on the measured first optical absorption and the measured second optical absorption.

2. The method according to claim 1, wherein the compound having a 4-(1H-pyrrol-2-yl)pyridine ligand structure is 4-(1H-pyrrol-2-yl)pyridine.

3. The method according to claim 1, wherein the compound having a 4-(1H-pyrrol-2-yl)pyridine ligand structure is immobilized on a solid support.

4. The method according to claim 1, wherein the compound having a 4-(1H-pyrrol-2-yl)pyridine ligand structure is bound to a polymer.

5. The method according to claim 2, wherein the change of the optical absorption is measured at a 463 nm absorption peak of an absorption spectrum of the 4-(1H-pyrrol-2-yl)pyridine.

6. The method according to claim 2, wherein the aqueous analyte is selected from the group consisting of a food, a wine, a juice, a beer, a cider, a chemical solution, an environmental sample, and a pharmaceutical product.

7. The method according to claim 2, wherein said measuring comprises determining an absorption spectrum within an optical wavelength range.

8. The method according to claim 2, wherein the aqueous analyte has a pH of between 2 and 10.

9. The method according to claim 2, further comprising calculating an amount of free sulfite in the aqueous analyte.

10. The method according to claim 9, further comprising pH-compensating the calculation of the amount of free sulfite in the aqueous analyte.

11. The method according to claim 9, further comprising adjusting a pH the aqueous analyte.

12. The method according to claim 2, wherein the aqueous analyte is added to the compound in a quantity sufficient to bleach the 4-(1H-pyrrol-2-yl)pyridine by 10% at 463 nm.

13. The method according to claim 2, wherein the compound is provided as an aqueous solution of 0.022 M 4-(1H-pyrrol-2-yl)pyridine.

14. An apparatus for performing a method for detecting a free sulfite in an aqueous analyte, comprising:

reacting the free sulfite in the aqueous analyte, with 4-(1H-pyrrol-2-yl)pyridine, having an optical absorption and being subject to bleaching by free sulfite; and determining a colorimetric change resulting from the reacting, comprising measuring a change of the optical absorption by reaction of the free sulfite in the aqueous analyte with the 4-(1H-pyrrol-2-yl)pyridine, the apparatus comprising:

a spectrometer;

a fluidic device configured to add the aqueous analyte in a sufficient quantity to bleach the 4-(1H-pyrrol-2-yl)pyridine by 10% at 463 nm; and a calculation device, configured to determine and output a concentration of the free sulfite in the aqueous analyte based on the bleaching of 4-(1H-pyrrol-2-yl)pyridine determined by the spectrometer.

15. The apparatus according to claim 14, wherein the spectrometer comprises a spectrophotometer which measures optical absorption at 463 nm.

16. The apparatus according to claim 14, further comprising at least one of a pH sensor and a pH titrator, wherein the determination of the concentration of sulfite is pH compensated.

17. The apparatus according to claim 14, having a practical lower limit of quantification of 0.84 ppm.

18. The apparatus according to claim 14, wherein the calculation device comprises a smartphone, further comprising a downloadable colorimeter app for the smartphone, adapted to access hardware and resources of the smartphone for determining a colorimetric change corresponding to the concentration of sulfite in the aqueous analyte.

19. A method of determining a free sulfite concentration in an aqueous analyte, comprising:

providing 4-(1H-pyrrol-2-yl)pyridine, adding a first amount of the aqueous analyte to the 4-(1H-pyrrol-2-yl)pyridine, and measuring a first bleaching of an optical absorption of the 4-(1H-pyrrol-2-yl)pyridine;

adding a second amount of the aqueous analyte to the 4-(1H-pyrrol-2-yl)pyridine after the first bleaching, and measuring a second bleaching of an optical absorption of the 4-(1H-pyrrol-2-yl)pyridine, and calculating the free sulfite concentration in the aqueous analyte based on at least the second bleaching.

20. The method according to claim 19, wherein the optical absorption is measured at 463 nm with an absorption spectrometer, further comprising at least one of:

pH-compensating the calculation of the amount of free sulfite in the aqueous analyte, and pH-adjusting the aqueous analyte.

* * * * *